US009216235B2

(12) United States Patent
Brownlee et al.

(10) Patent No.: US 9,216,235 B2
(45) Date of Patent: Dec. 22, 2015

(54) PHOTOACTIVATED CROSSLINKING OF A PROTEIN OR PEPTIDE

(75) Inventors: Alan George Brownlee, Salisbury (AU); Christopher Malcolm Elvin, Tennyson (AU); Jerome Anthony Werkmeister, Camberwell (AU); John Alan Maurice Ramshaw, Pascoe Vale (AU); Charles Mark Lindall, Killara (AU)

(73) Assignee: Cook Medical Technologies LLC, Bloomington, IN (US)

( * ) Notice: Subject to any disclaimer, the term of this patent is extended or adjusted under 35 U.S.C. 154(b) by 477 days.

(21) Appl. No.: 12/673,400

(22) PCT Filed: Aug. 14, 2008

(86) PCT No.: PCT/AU2008/001178
§ 371 (c)(1),
(2), (4) Date: Feb. 12, 2010

(87) PCT Pub. No.: WO2009/021287
PCT Pub. Date: Feb. 19, 2009

(65) Prior Publication Data
US 2011/0190813 A1 Aug. 4, 2011

(30) Foreign Application Priority Data

Aug. 14, 2007 (AU) .................................. 2007904359
Aug. 14, 2007 (AU) .................................. 2007904381
Mar. 31, 2008 (AU) .................................. 2008901531

(51) Int. Cl.
*A61L 24/10* (2006.01)
*A61L 24/00* (2006.01)
*A61L 26/00* (2006.01)
*A61L 27/22* (2006.01)
*A61L 27/50* (2006.01)
*C08H 1/00* (2006.01)
*C09J 189/00* (2006.01)

(52) U.S. Cl.
CPC ............... *A61L 24/10* (2013.01); *A61L 24/001* (2013.01); *A61L 24/0026* (2013.01); *A61L 26/0028* (2013.01); *A61L 26/0061* (2013.01); *A61L 26/0076* (2013.01); *A61L 27/22* (2013.01); *A61L 27/50* (2013.01); *C08H 1/00* (2013.01); *C09J 189/00* (2013.01)

(58) Field of Classification Search
CPC ........................................................ A61L 24/10
USPC ............... 606/213–215; 436/524–525; 424/443–445, 447; 128/898
See application file for complete search history.

(56) References Cited

U.S. PATENT DOCUMENTS

| 4,474,851 | A | 10/1984 | Urry |
|---|---|---|---|
| 5,713,891 | A * | 2/1998 | Poppas ............................. 606/2 |
| 6,509,031 | B1 * | 1/2003 | Miller et al. ................... 424/443 |
| 6,607,522 | B1 * | 8/2003 | Hamblin et al. .................. 606/8 |
| 6,613,582 | B1 * | 9/2003 | Kodadek et al. ............... 436/524 |
| 6,875,427 | B1 * | 4/2005 | DeVore et al. ............. 424/78.03 |
| 6,875,796 | B2 * | 4/2005 | Stedronsky .................... 523/118 |
| 2006/0286063 | A1 * | 12/2006 | Shebuski et al. ............. 424/78.3 |
| 2007/0275408 | A1 * | 11/2007 | Elvin ............................. 435/7.1 |
| 2009/0162896 | A1 * | 6/2009 | Scheibel ...................... 435/69.1 |

FOREIGN PATENT DOCUMENTS

| WO | WO 03/037248 | 5/2003 |
| WO | WO 2004/104042 | 12/2004 |
| WO | WO 2007/057207 | * 5/2007 ........... C07K 14/435 |
| WO | WO 2007/092998 | 8/2007 |

OTHER PUBLICATIONS

Fancy et al., 2000, Scope, limitations and mechanistic aspects of the photo-induced cross-linking of proteins by water-soluble metal complexes, Chemistry & Biology, 7(9), 697-708.*
International Search Report and Written Opinion for PCT Application No. PCT/AU2008/001178, 11 pages, Sep. 5, 2009.
International Preliminary Report on Patentability for PCT Application No. PCT/AU2008/001178, 9 pages, Feb. 25, 2010.
Barnes CP, Smith MJ, Bowlin GL, Sell SA, Tang T, Matthews JA, Simpson DG, Nimtz JC "Feasibility of Electrospinning the Globular Proteins Hemoglobin and Myoglobin" Journal of Engineered Fibers and Fabrics vol. 1 No. 2, 16-29 (2006).
Brown, KC and Kodadek, T Met Ions Biol Syst. 2001;38:351-84. "Protein cross-linking mediated by metal ion complexes".
Dickneite, G., H. J. Metzner, M. Kroez, et al. "The Importance of Factor XIII as a Component of Fibrin Sealants." Journal of Surgical Research 107 (Oct. 2002): 186-195.
Dodd, R. A., R. Cornwell, N. E. Holm, et al. "The Vivostat Application System: A Comparison with Conventional Fibrin Sealant Application Systems." Technology and Health Care 10 (2002): 401-411.
D A. Fancy and T. Kodadek "Chemistry for the analysis of protein—protein interactions: Rapid and efficient cross-linking triggered by long wavelength light." Proc. Natl. Acad. Sci. vol. 96, pp. 6020-6024, May 1999.
David A Fancy, Carilee Denison, Kyonghee Kim, Yueqing Xie, Terra Holdeman, Frank Amini and Thomas Kodadek "Scope, limitations and mechanistic aspects of the photo-induced cross-linking of proteins by water-soluble metal complexes" Chemistry & Biology (2000) 7:697-708.
Furst W, Banerjee A, Redl H. Comparison of structure, strength and cytocompatibility of a fibrin matrix supplemented either with tranexamic acid or aprotinin. J Biomed Mater Res B Appl Biomater. (2007) 82:109-14.

(Continued)

Primary Examiner — Amber D Steele
(74) Attorney, Agent, or Firm — Woodard Emhardt Moriarty McNett & Henry LLP

(57) ABSTRACT

A method of crosslinking a protein or peptide for use as a biomaterial, the method comprising the step of irradiating a photoactivatable metal-ligand complex and an electron acceptor in the presence of the protein or peptide, thereby initiating a crosslinking reaction to form a 3-dimensional matrix of the biomaterial.

14 Claims, 22 Drawing Sheets

(56) References Cited

OTHER PUBLICATIONS

Jackson, M. R. "Fibrin Sealants in Surgical Practice: An Overview." American Journal of Surgery 182 (Aug. 2001) (2 Suppl): 1S-7S.

Khadem, J., Veloso, A.A., Tolentino, F.T., Hasan, T. and Hamblin, M.R., "Photodynamic Tissue Adhesion with Chlorine6, Protein Conjugates". IOVS, Dec. 1999, vol. 40, No. 13.

Kodadek T, Isabelle Duroux-Richard and Jean-Claude Bonnafous, ."Techniques: Oxidative cross-linking as an emergent tool for the analysis of receptor-mediated signalling events." Trends in Pharmacological Sciences vol. 26 No. 4 Apr. 2005.

Lee, K-C, Park, S-K and Lee, K-S (1991) "Neurosurgical applications of fibrin adhesive." 9th Annual congress of the world society of cardio-thoracic surgeons; Nov. 1999, Lisbon, Spain.

Lee MG, Jones D. "Applications of fibrin sealant in surgery." Surg Innov. 2005; 12:203-213.

Makogonenko E, Ingham KC, Medved L. Interaction of the fibronectin COOH-terminal Fib-2 regions with fibrin: further characterization and localization of the Fib-2-binding sites. Biochemistry. May 8, 2007;46(18):5418-26. Epub Apr. 11, 2007.

Mankad, P. S., and M. Codispoti. "The Role of Fibrin Sealants in Hemostasis." American Journal of Surgery 182 (Aug. 2001) (2 Suppl): 21S-28S.

Marone Piero, Monzillo Vincenza, Segu Catia, Antoniazzi Elena, "Antibiotic-Impregnated Fibrin Glue in Ocular Surgery:In vitro Antibacterial Activity", Ophthalmologica 1999; 213:12-15.

Matras, H (1985) Fibrin seal: the state of the art. J Oral Maxillofac Surg 43: 605-611.

McManus, M, Sell SA, Espy PG, Koo, HP and Bowlin GL (2006) "On the Road to in situ Tissue Regeneration: A Tissue Engineered Nanofiber Fibrinogen-Polydioxanone Composite Matrix" (Abstract) Proceedings of Mid-Atlantic section of the American Urological Association Annual Meeting, 2006 http://www.maaua.org/abstracts/2006/07.cgi.

Milne, AA, Murphy, WG, Reading, SJ and Ruckley, CV (1995) Fibrin sealant reduces suture line bleeding during carotid endarterectomy: a randomised trial. Eur J Endovasc Surg 10: 91-94.

Morikawa, T. "Tissue Sealing." American Journal of Surgery 182 (Aug. 2001) (2 Suppl): 29S-35S.

Mosesson MW. Fibrinogen and fibrin structure and functions. J Thromb Haemost. (2005) 3:1894-904.

Mosesson MW, Siebenlist KR, Meh DA. The structure and biological features of fibrinogen and fibrin. Ann NY Acad Sci. 2001;936:11-30.

Nishimoto Kazuo, Yamamura Keiko, Fukase Fumiaki, Kobayashi! Masayoshi, Nishikimil Naomichi and Komoril Kimihiro, "Subcutaneous tissue release of amikacin from a fibrin glue/polyurethane graft", Journal of Infection and Chemotherapy; vol. 10, No. 2 (2004) pp. 101-104.

Velada JL, Hollingsbee DA, Menzies AR, Cornwell R, Dodd RA. Reproducibility of the mechanical properties of Vivostat system patient-derived fibrin sealant. Biomaterials. May 2002;23(10):2249-54.

Weisel JW, "Fibrinogen and fibrin", Adv Protein Chem. 2005;70:247-299.

Yoshida H, Yamaoka, Y., Shinoyama M., Biol Pharm Bull. 2000; pp. 371-374 "Novel drug delivery system using autologous fibrin glue-release properties of anti cancer drugs", Department of Pharmacy, Yamaguchi University Hospital, Ube, Japan.

Communication from European Patent Office issued in related application PCT/AU2008/001178 dated Nov. 15, 2012.

\* cited by examiner

PHOTOACTIVATED CROSSLINKING OF A PROTEIN OR PEPTIDE

This application is a filing under 35 U.S.C. §371 of International Patent Application PCT/AU2008/001178, filed Aug. 14, 2008, which claims priority to Australian Application No. 2007904359, filed Aug. 14, 2007, Australian Application No. 2007904381, filed Aug. 14, 2007, and Australian Application No. 2008901531, filed Mar. 31, 2008.

TECHNICAL FIELD

The present invention relates to photoactivated crosslinking of a protein or peptide to form a biomaterial and, more particularly, to the preparation of a manufactured article of cross-linked proteinaceous material, the manufacture of such materials and their uses. Without limitation, in embodiments the invention relates to a peptidic or proteinaceous scaffold for tissue engineering and methods for the use of such a scaffold. The present invention additionally relates to a method of adhesion or the joining and/or sealing tissues involving administration of a photoactivatable composition in surgical procedures and medical methods, and compositions for use in said methods. The present invention additionally relates to a method of joining and/or sealing non-biological materials and compositions for use for this purpose.

BACKGROUND ART

Tissue engineering including the use of biomaterials offers a novel route for repairing damaged or diseased tissues by incorporating the patients' own healthy cells or donated cells into temporary housings or scaffolds as well as sealing and/or joining severed tissues. The structure and properties of the scaffold are critical to ensure normal cell behaviour and performance of the cultivated or repaired tissue. Biomaterials play a crucial role in such schemes by offering flexible design opportunities, directing subsequent cellular behaviour or function, as well as facilitating resorption rates and ultimate tissue form and strength.

A range of approaches has been used for the construction and assembly of such biomaterials, including the use of a number of synthetic materials, but it is clear that materials from natural sources are superior because of their inherent properties of biological recognition, and their susceptibility to cell-triggered proteolytic breakdown and remodelling.

Natural protein such as extracellular matrix (ECM) proteins show promise in tissue engineering applications because of their biocompatibility, but have been found to be lacking in many areas as a result of inappropriate physical properties. For example, McManus et al (2006) have found that electrospun fibrinogen has insufficient structural integrity for implantation, and instead employed an electrospun fibrinogen-polydioxanone (PDS) composite scaffold for urinary tract reconstruction. Fibrinogen, collagen, elastin, haemoglobin and myogloglobin are reported to have been electrospun (Barnes et al, 2006). The electrospinning process involves imparting a charge to a polymer solution (or melt) and drawing the charged solution into a nozzle. As the electrostatic charges within the solution overcome the surface tension, a liquid jet is initiated at the nozzle. The liquid jet is directed to a rotating mandrel some distance away. As the solution travels the solvent evaporates, and a film is deposited on the mandrel, thus a non-woven, fibrous mat is produced. Additionally, fibrin microbeads and nanoparticles are described in WO 03/037248 (Hapto Biotech, Inc.) and comprise beads of fibrinogen and thrombin manufactured by mixing an aqueous solution of fibrinogen, thrombin and Factor XIII and oil at 50-80 C to form an emulsion. To form nanoparticles the emulsion so-formed is homogenised and the nanoparticles isolated by filtration as a fibrin clot created following cleavage of fibrinogen under the influence of thrombin and Factor VIII. However, these beads and fibres are limited in their shape configuration and flexibility.

Biomaterials such as tissue adhesives have been suggested as alternatives in surgical procedures to physical procedures of connecting tissues such as sutures and staples. Tissue adhesives will hold cut or separated areas of tissue together to allow healing and/or serve as a barrier to leakage, depending on the application. The adhesive should break down or be resorbed and it should not hinder the progress of the natural healing process.

Ideally, the agent should promote the natural mechanism of wound healing and then degrade.

Tissue adhesives are generally utilized in three categories:
  i) Hemostasis (for example, by improving in vivo coagulation systems, tissue adhesion itself has a hemostatic aim and it is related to patient clotting mechanisms)
  ii) Tissue sealing: primary aim is to prevent leaks of various substances, such as air or lymphatic fluids.
  iii) Local delivery of exogenous substances such as medications, growth factors, and cell lines.

One accepted value of fibrin glues lies in their unique physiologic action, which mimics the early stages of the blood coagulation process and wound healing; the part of the normal coagulation cascade to produce an insoluble fibrin matrix. Fibrinogen is a plasma protein which is naturally cleaved to soluble fibrin monomers by the action of activated thrombin. These monomers are cross-linked into an insoluble fibrin matrix with the aid of activated factor XIII. The adhesive qualities of consolidated fibrin sealant to the tissue may be explained in terms of covalent bonds between fibrin and collagen, or fibrin, fibronectin and collagen. Fibrin glues act as both a hemostatic agent and as a sealant. They are bioabsorbable (due to in vivo thrombolysis). Degeneration and reabsorption of the resulting fibrin clot is achieved during normal wound healing.

All fibrin sealants in use as of 2008 have multi-component having two major ingredients, fibrinogen and thrombin and optionally human blood factor XIII and a substance called aprotinin, which is derived from cows' lungs. Factor XIII is a compound that strengthens blood clots by forming covalent cross-links between strands of fibrin. Aprotinin is a protein that inhibits the enzymes that break down blood clots. However these sealants being multicomponent require double barrelled syringes, reconstitution of the multiple components and require exquisite mixing during application to give rise to a uniform and efficious glue.

In an effort to develop a single component protein derived biomaterial, purified thrombin has been developed and now marketed to controlling bleeding during surgery. Upon its application to the tissue site the thrombin cleaves endogenous fibrinogen to produce fibrin in vivo. It is well known that fibrin (which forms the fibrillar matrix on thrombin cleavage of fibrinogen) self-associates (Mosesson MW (2005) Mosesson et al MW, 2001). Factor XIII may be co-administered, and causes dimerisation of the 7-chain of fibrinogen in association with its cleavage by thrombin (Furst W, et al (2007). The success of the procedure relies upon Factor XIII-mediated crosslinking (Lee M G and Jones D (2005) to stabilise the thrombin-derived clot, and a process of stabilising the clot which does not rely on the presence of Factor XIII would be desirable. This single component biomaterial is limited in its applicability, can practically only be used for small bleeds, and the resultant clot, which is slow to form typically has low mechanical strength.

Despite the availability of all of these different biomaterials for the surgeon to use in various surgical procedures there still remains a need for a simple biomaterial that is tunable in its mechanical and biological properties, is easy to use and apply and can be used in a variety of applications for a variety of diseases and surgical procedures.

SUMMARY OF THE INVENTION

In one aspect there is provided a method of crosslinking a protein or peptide for use as a biomaterial, the method comprising the step of irradiating a photoactivatable metal-ligand complex and an electron acceptor in the presence of the protein or peptide, thereby initiating a cross-linking reaction to form a 3-dimensional matrix of the biomaterial.

In a further aspect there is provided a biomaterial comprising a 3-dimensional matrix of a protein or peptide crosslinked through irradiation a photoactivatable metal-ligand complex and an electron acceptor in the presence of the protein or peptide, thereby initiating a cross-linking reaction to form a 3-dimensional matrix of the biomaterial.

In a still further aspect there is provided a method of joining and/or sealing tissues in a surgical procedure or medical treatment, comprising the steps of:

(1) applying to a tissue portion a photoactivatable metal-ligand complex and an electron acceptor and optionally an at least partially denatured protein (2) irradiating said tissue portion to photoactivate the photoactivatable metal-ligand complex;

thereby initiating a cross-linking reaction between (a) one or more endogenous proteins and/or (b) said at least partially denatured protein to seal said tissue portion or join said tissue portion to an adjacent tissue portion and wherein said at least partially denatured protein has been rendered more susceptible to photochemical cross-linking compared to its native state In a still further aspect there is provided a closure for a leaking wound comprising a substrate suitable for application to a wound to stem leakage, wherein said substrate is impregnated or coated with a photoactivatable metal-ligand complex and an electron acceptor or with an at least partially denatured protein, a photoactivatable metal-ligand complex and an electron acceptor, wherein said at least partially denatured protein has been rendered more susceptible to photochemical cross-linking compared to its native state.

In a yet another aspect there is provided the use of thrombin, a photoactivatable metal-ligand complex and an electron acceptor for joining and/or sealing tissues.

In a yet another aspect there is provided the use of a photoactivatable complex and an electron acceptor for joining and/or sealing tissues.

In a yet another aspect there is provided a composition comprising an at least partially denatured protein, a photoactivatable metal-ligand complex and an electron acceptor, wherein said at least partially denatured protein or chemically modified protein has been rendered more susceptible to photochemical cross-linking compared to its native state.

In a yet another aspect there is provided the use of an at least partially denatured protein, a photoactivatable metal-ligand complex and an electron acceptor for joining and/or sealing tissues.

In a yet another aspect there is provided the use of a protein or peptide, a photoactivatable metal-ligand complex and an electron acceptor for joining and/or sealing substrates.

| Lane No. | Sample |
| --- | --- |
| 1 | 0 secs |
| 2 | 1 sec |
| 3 | 2 sec |
| 4 | 5 sec |
| 5 | 10 sec |
| 6 | 30 sec |
| 7 | 60 sec |
| 8 | Protein size standards |

Figure 2:
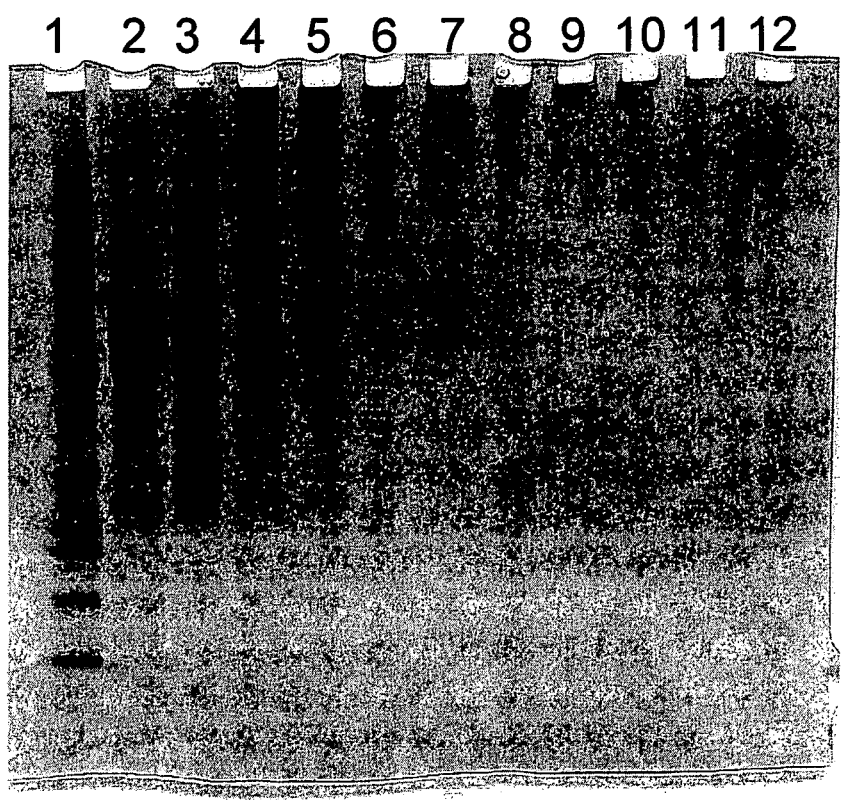

FIG. 2 shows a photograph of an electrophoresis gel in which reactions mixtures containing 25 µg of bovine fibrinogen (Sigma); 20 mM persulfate (Sodium salt) and various concentrations of [Ru(bpy)$_3$]Cl$_2$, all in 25 µl PBS, were exposed to 300 W incoherent light from Quartz Halogen dichroic source for 1 min.

| Lane No. | Sample |
| --- | --- |
| 1. | MW Standards (as above) |
| 2. | 2 mM [Ru(bpy)$_3$]Cl$_2$, No Light |
| 3. | 0 [Ru(bpy)$_3$]Cl$_2$ |
| 4. | 0 NaPS |
| 5. | 1 µM |
| 6. | 5 µM |
| 7. | 10 µM |
| 8. | 25 µM |
| 9. | 50 µM |
| 10. | 100 µM |
| 11. | 500 µM |
| 12. | 2000 µM |

Figure 3:
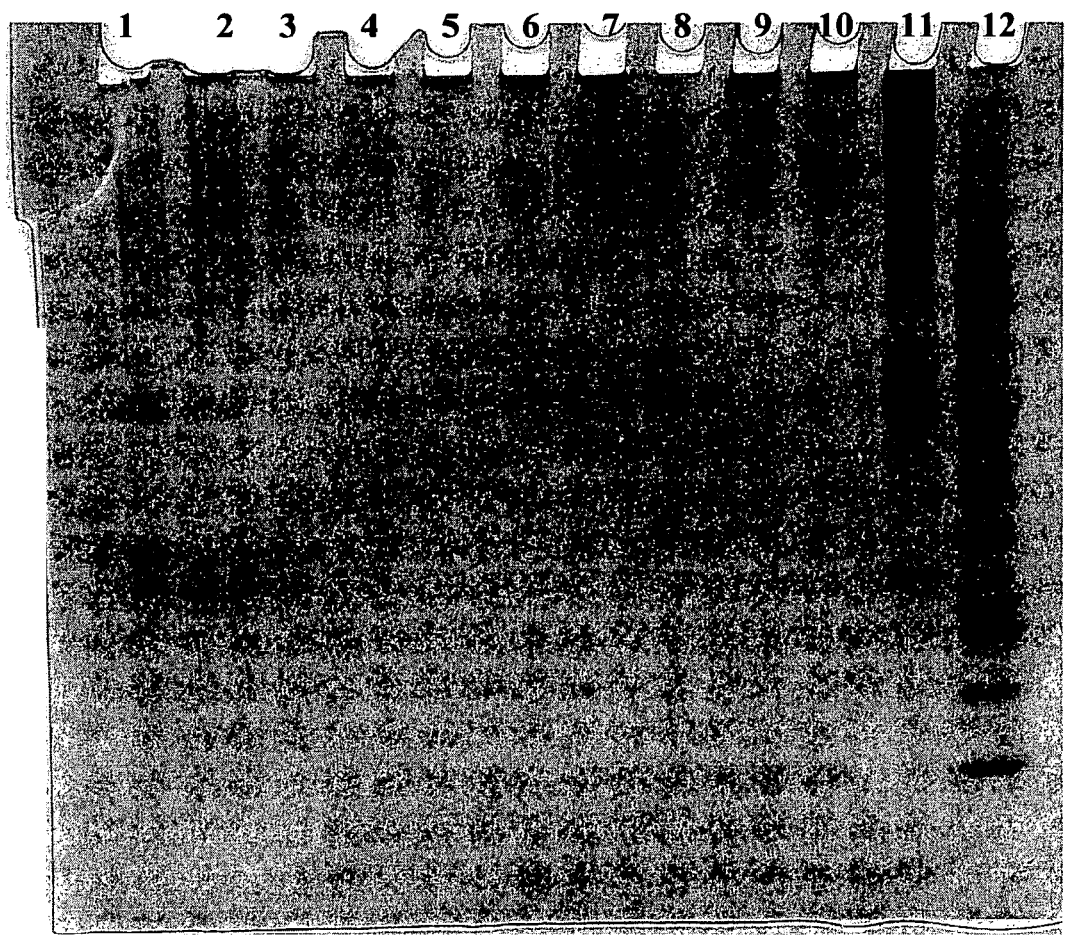

FIG. 3 shows a photograph of an electrophoresis gel in which reaction mixtures containing 25 µg of bovine fibrinogen (Sigma); 2 mM [Ru(bpy)$_3$]Cl$_2$ (Aldrich) all in 25 µl PBS. (SPS: sodium persulfate; APS: ammonium persulfate) were exposed to 300 W incoherent light from Quartz Halogen dichroic source for 1 min.

| Lane No. | Sample |
| --- | --- |
| 1. | 20 mM SPS |
| 2. | 10 mM SPS |
| 3. | 5 mM SPS |
| 4. | 2.5 mM SPS |
| 5. | 1.25 mM SPS |
| 6. | 0.63 mM SPS |
| 7. | 0.31 mM SPS |
| 8. | 10 mM APS |
| 9. | 2.5 mM APS |
| 10. | 0.63 mM APS |
| 11. | 0 persulfate |
| 12. | MW Standards. (as above) |

Figure 4:
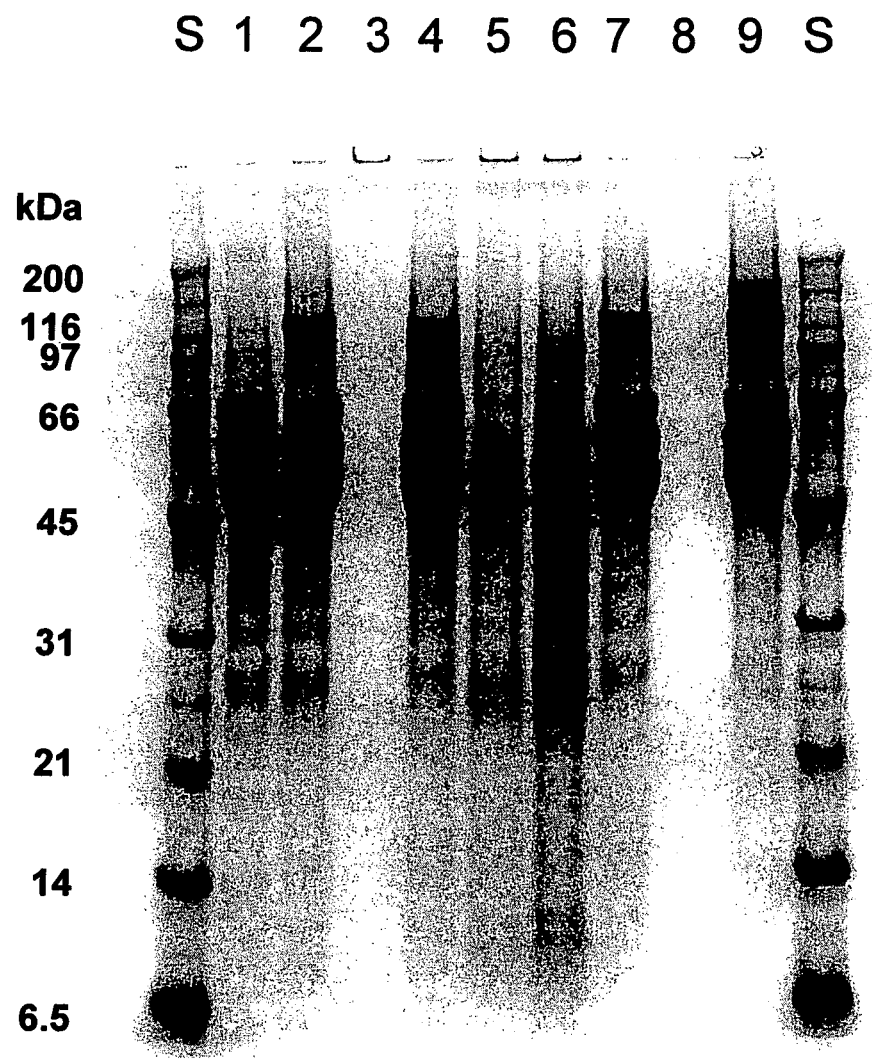
Figure 5:
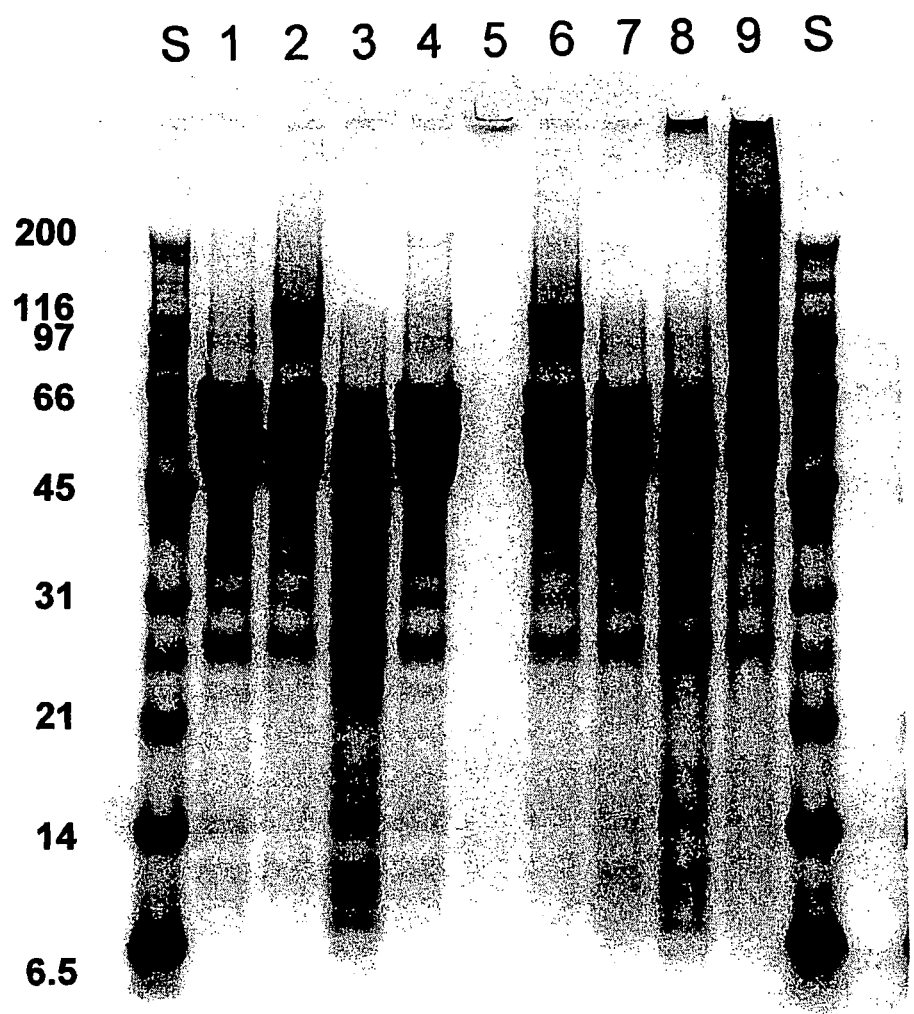

FIG. 4 is an electrophoresis gel showing the results of cross-linking when alternative electron acceptors (oxidants) are employed, in which the lanes are as follows:

S. Protein Standard
Fib+2 mM Ru2+only
Fibrinogen only
Fib+2 mM Ru2++NaPS
Fib+2 mM Ru2++Vit B12
Fib+2 mM Ru2++Cerium Sulphate
Fib+2 mM Ru2++Cerium Nitrate
Fib+2 mM Ru2++Oxalic acid
Fib+2 mM Ru2++Na-Periodate
Fib+2 mM Ru2++EDTA FIG. 5 is a gel showing the results of cross-linking using alternative metal-ligand complexes (catalysts), in which the lanes are as follows:
S. Protein Standard
Fibrinogen only
Fib+1 mM Ru2+only
Fib+10 mM NaPS only
Fib+10 mM H2O2 only
Fib+1 mM Ru2++10 mM NaPS
Fib+1 mM Ru2++10 mM H2O2
Fib+1 mM Hemin only
Fib+1 mM Hemin+10 mM NaPS
Fib+1 mM Hemin+10 mM H2O2

Figure 6:
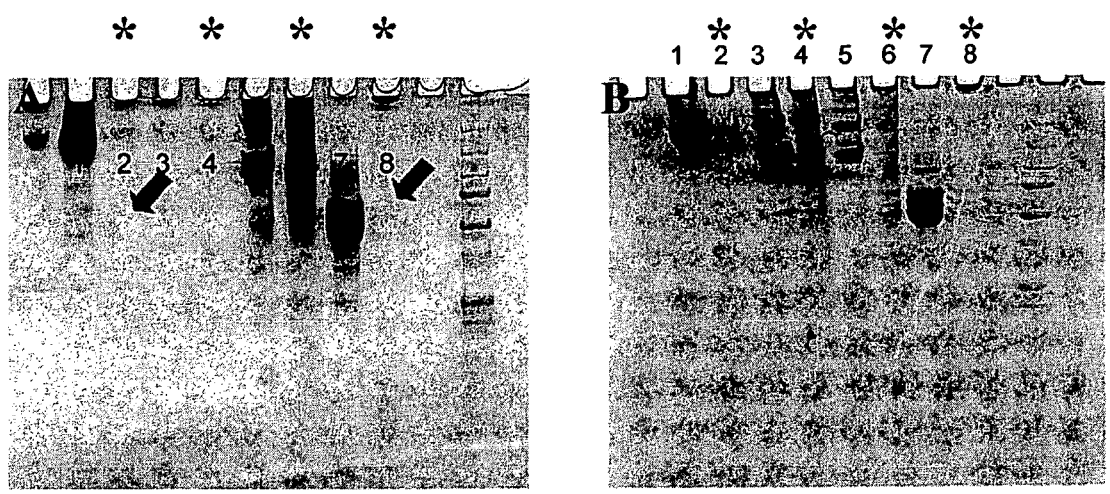

FIG. 6 shows a photograph of an electrophoresis gel that demonstrates ruthenium-catalysed photo-crosslinking of the additional matrix proteins fibronectin and collagen.
Lanes:
Gel A:
1. horse fibronectin
2. horse fibronectin crosslinked with [Ru(bpy)$_3$]Cl$_2$
5. Devro medical collagen (4 mg/ml); kangaroo tail
6. Devro medical collagen (4 mg/ml); kangaroo tail, crosslinked with [Ru(bpy)$_3$]Cl$_2$
7. bovine fibrinogen
8. bovine fibrinogen crosslinked with [Ru(bpy)$_3$]Cl$_2$
Gel B:
1. horse fibronectin
2. horse fibronectin crosslinked with [Ru(bpy)$_3$]Cl$_2$
3. Devro medical collagen (4 mg/ml); kangaroo tail
4. Devro medical collagen (4 mg/ml); kangaroo tail, crosslinked with [Ru(bpy)$_3$]Cl$_2$
5. Chicken collagen
6. Chicken collagen crosslinked with [Ru(bpy)$_3$]Cl$_2$
7. bovine fibrinogen
8. bovine fibrinogen crosslinked with [Ru(bpy)$_3$]Cl$_2$.

Figure 7:
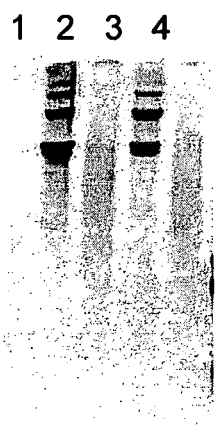

FIG. 7 demonstrates the rapid and efficient cross-linking of soluble collagen solutions using the photochemical process. Collagen in solution (Devro) was cross-linked using Ruthenium complex and white light for 30 secs then run on 10% PAGE in denaturing conditions:
1. Kangaroo Tail Collagen 20 µg
2. Kangaroo Tail Collagen 20 µg Ruthenium cross-linked
3. Calf Skin Collagen 20 µg
4. Calf Skin Collagen 20 µg Ruthenium cross-linked revealing the very high MW collagen polymer formed after 30 secs illumination (lanes 2,4)

Figure 8:
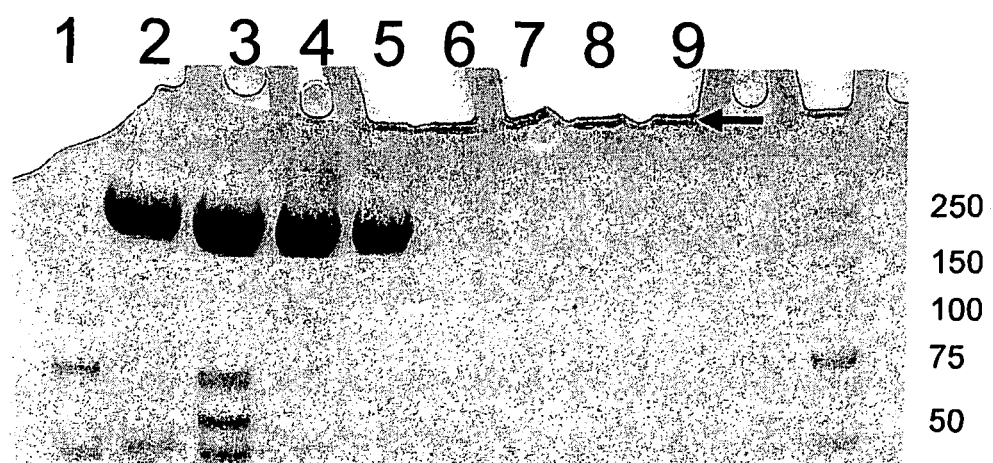

FIG. 8 demonstrates the highly efficient cross-linking of fibronectin using the photochemical process. Bovine fibronectin was purified from bovine plasma cryoprecipitate using gelatin-agarose chromatography, eluted with 3M urea. Shown are 4 different fibronectin-rich fractions from the purification (lanes 2, 3, 4, 5) and the same following cross-linking with Ru chemistry for 20 secs (lanes 6-9). Lanes 3 and 7 shows that traces of fibrinogen present in that particular fraction also participates in the reaction.

Figure 9:
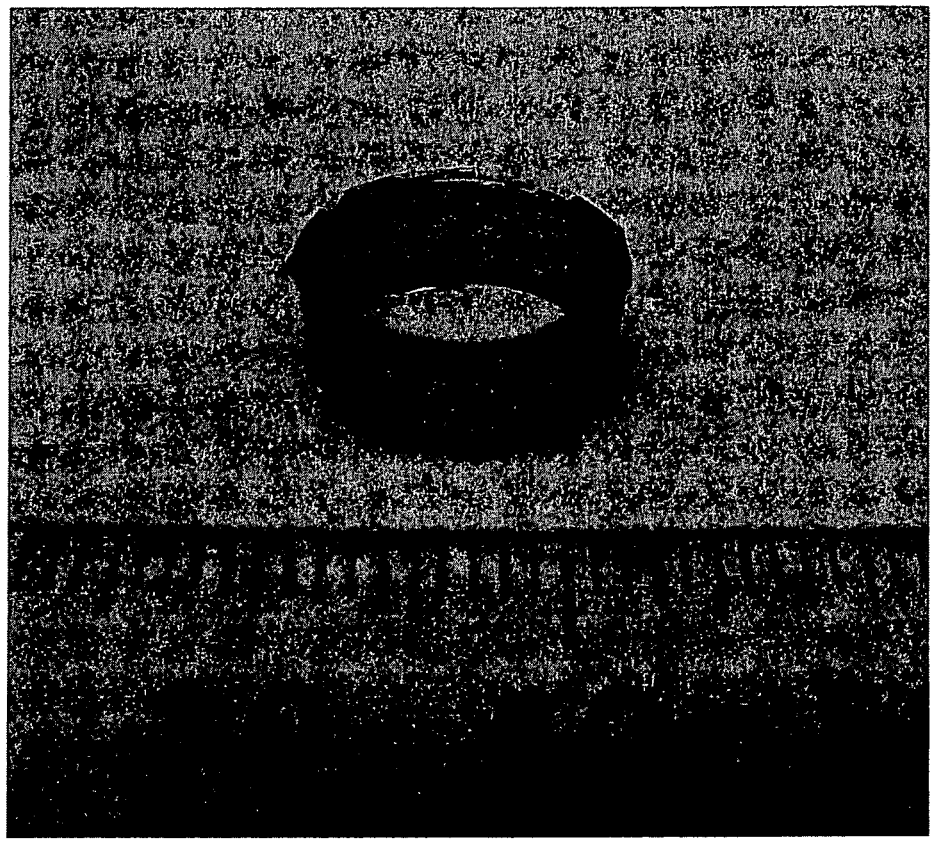

FIG. 9 demonstrates the casting of a 3-D structure from fibrinogen, potentially serving as an implantable biocompatible prosthesis or scaffold. Fibrinogen solution (150 mg/ml) mixed with Ruthenium complex was cast in a Lucite mould and illuminated for 30 secs with white light. Scale rule marked in mm.

Figure 10:

FIG. 10 demonstrates a solid lens-shaped structure cast from collagen solution. A solution of bovine collagen (1%) was cast in a glass hemispherical well and cross-linked using Ru chemistry then dialysed against PBS for 24 hours.

Figure 11:
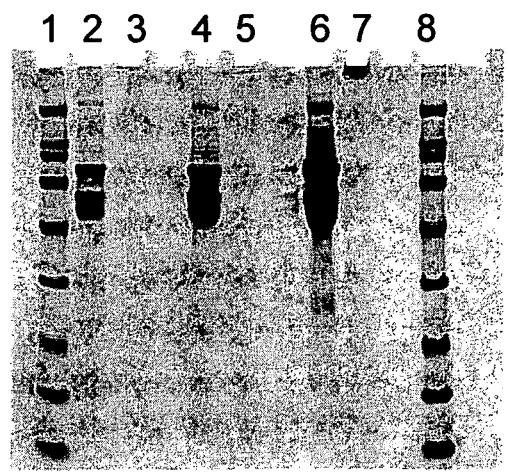

FIG. 11 demonstrates using gel electrophoresis the highly rapid and efficient cross-linking of soluble fibrinogen. 4 mg/ml Pig Fibrinogen (Sigma) was cross-linked for 30 secs and run on Denaturing SDS-PAGE. Lanes 2, 4, 6: 10, 20, 50 microgram protein respectively; lanes 3, 5, 7 same after cross-linking. Lanes 1, 8: MW standards. All subunits of fibrinogen participate in the cross-linking reaction.

Figure 12:
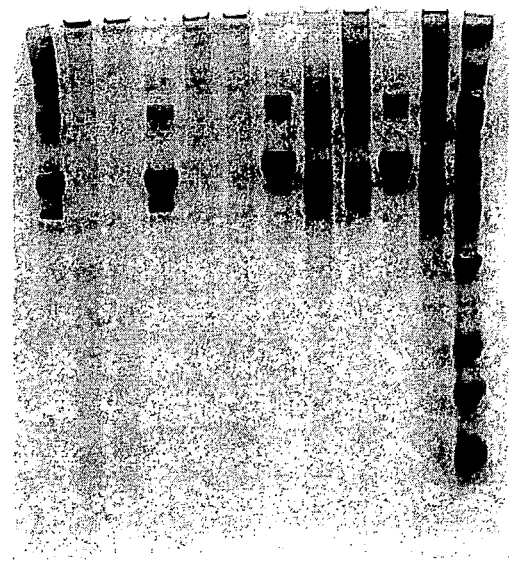

FIG. 12 demonstrates the cross-linking of soluble denatured bovine serum albumin (BSA) Bovine serum albumin (BSA) at two concentrations (1 and 4 mg/ml) was dissolved in two buffers (50 mM sodium Acetate pH 4.0 or 50 mM tris-glycine, pH 9.0). Samples were heat denatured at 80 deg. for 60 min. Gel shows various BSA samples (native and denatured; cross-linked and uncross-linked; pH4.0 and pH9.0):
1. BSA 1 mg/ml Denatured pH 4.0 (1 hr, 80 deg C.)
2. BSA 1 mg/ml Denatured pH 4.0 Ruthenium cross-linked
3. BSA 4 mg/ml Denatured pH 4.0 Ruthenium cross-linked
4. BSA 1 mg/ml Native pH 4.0
5. BSA 1 mg/ml Native pH 4.0 Ruthenium cross-linked
6. BSA 4 mg/ml Native pH 4.0 Ruthenium cross-linked
7. BSA 1 mg/ml Denatured pH 9.0
8. BSA 1 mg/ml Denatured pH 9.0 Ruthenium cross-linked
9. BSA 4 mg/ml Denatured pH 9.0 Ruthenium cross-linked
10. BSA 1 mg/ml Native pH 9.0
11. BSA 4 mg/ml Native pH 9.0 Ruthenium cross-linked
12. Broad Range Standards Native and denatured BSA are cross-linked at pH 4.0 (lanes 2,3 and 5,6 respectively). Solid gels have also been prepared from 100 mg/ml BSA in buffer at pH4.0. At pH 9.0 native and denatured BSA are only incompletely reactive showing the effect of pH on the protein interaction.

Figure 13:
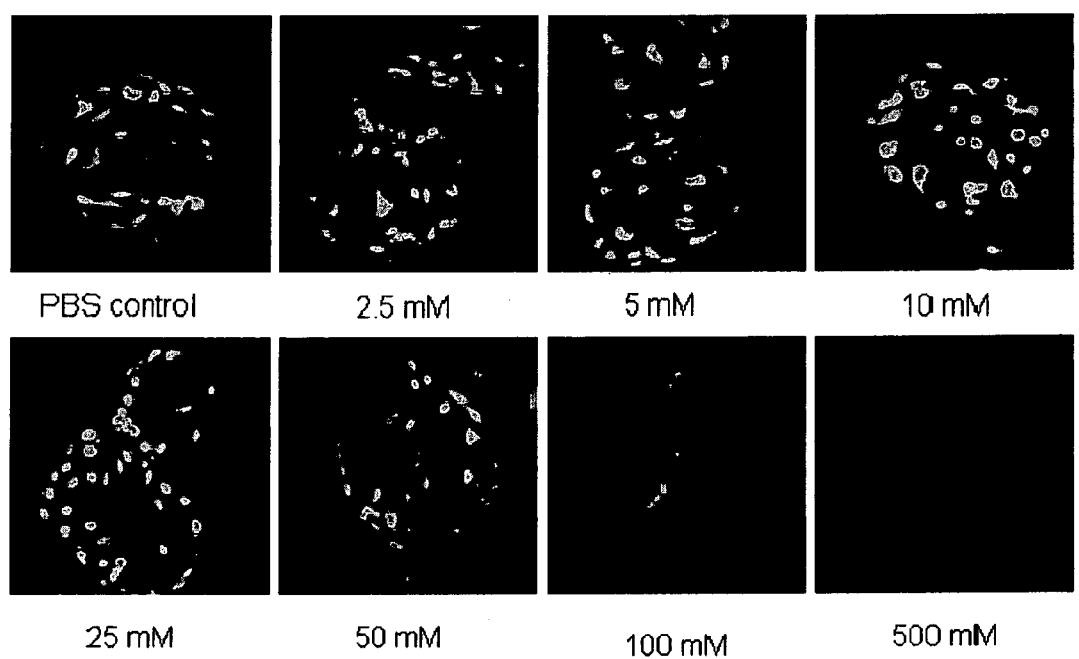

FIG. 13 demonstrates that cells (chondrocytes) exposed to sodium persulphate for 60 mins retain viability within a range persulphate levels. Human chondrocytic cells were pre-seeded onto Cultispher S beads. After growth for 6 days, an aliquot of cells on beads were incubated in PBS containing the above concentrations of sodium persulphate for 1 hr then washed 3 times in PBS and stained with calcein AM for live cells (green) and ethidium homodimer for dead cells (red).

Figure 14:
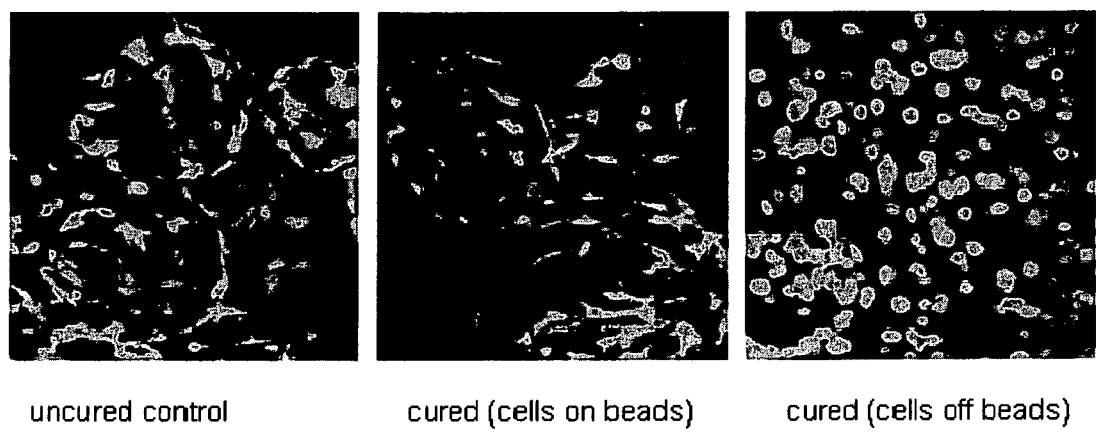

FIG. 14 demonstrates that cells (human chondrocytes) mixed with soluble porcine fibrinogen containing persulphate salt and Ru(Bpy)$_3$ retain viability at 60 minutes before and after photo-activated cross-linking. Human chondrocytic cells were pre-seeded onto Cultispher S beads. After growth for 7 days, an aliquot of cells on beads, along with cells alone (without beads) were mixed with porcine fibrinogen (200 mg/ml), 10 mM ammonium persulphate and 2 mM Ru(Bpy)$_3$. Mixtures of cells on beads or cells alone in fibrinogen containing the photochemical reagents were cross-linked with blue light (5×20 s) and cell viability in uncured and cross-linked constructs were assessed at 60 minutes using calcein AM for live cells (green) and ethidium homodimer for dead cells (red).

Figure 15:
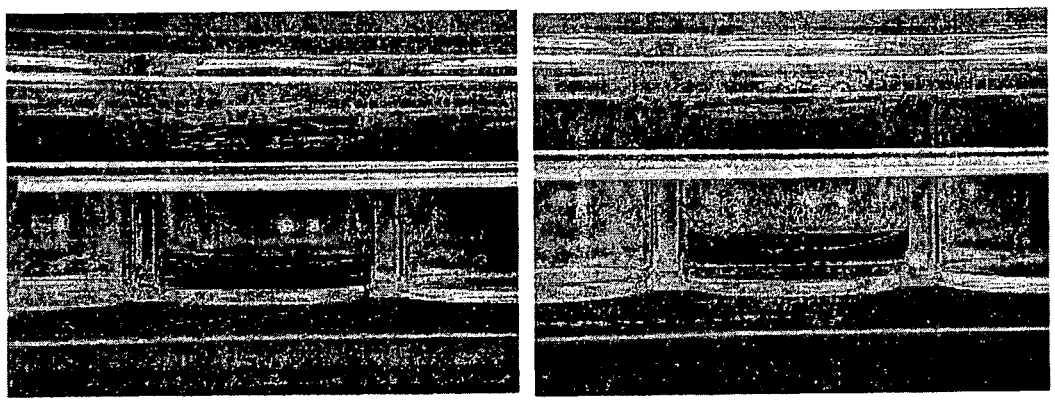

FIG. 15 demonstrates photo-activated cross-linking of gelatin into tissue culture scaffolds suitable for cell seeding. Various gelatin types (A,B) from bovine and porcine origin with varying bloom strengths were dissolved at 480 C for 24 to 48 hrs, the pH adjusted to 7.0-7.5, and filter sterilised using a 0.45 µm filter. In this figure porcine 300 bloom gelatin (~100 mg/ml) was mixed with 13.3 mM sodium persulphate and 1.3 mM Ru(Bpy)$_3$ and cross-linked with blue light (5×20 s). All solutions formed firm plugs that remained solid upon heating to 560 C (Day 0). Plugs were stable and remained sterile in PBS at 370 C up to 9 days.

Figure 16:
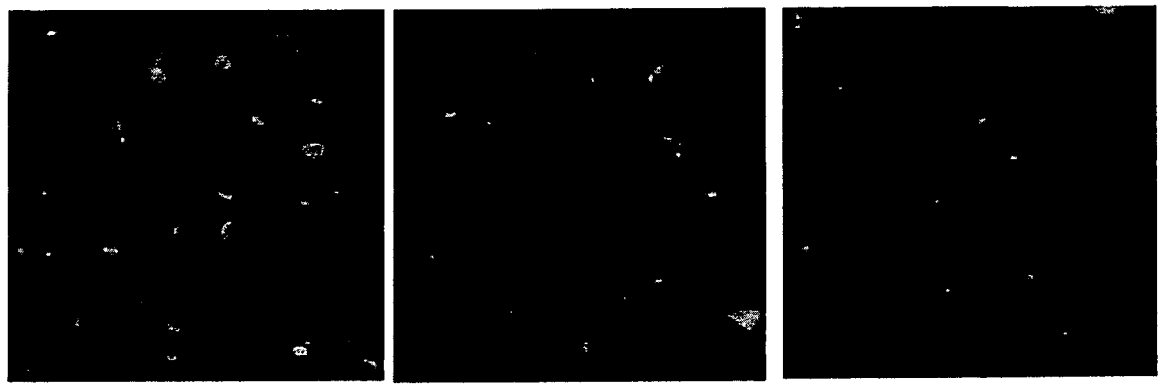

FIG. 16 demonstrates biocompatibility of photo-activated cross-linked gelatin plugs with mouse NR6 fibroblasts. Sterile gelatin plugs, prepared as described in FIG. 9, were seeded with 60×10$^3$ NR6 mouse fibroblasts in 1.2 ml DMEM culture medium containing 10% FBS in 24 well tissue culture plates, and incubated for 5 days at 370 C. Cells remained viable over the culture period with no signs of toxic, leachable compounds from the photochemical process. Cell viability was assessed using calcein AM for live cells (green) and ethidium homodimer for dead cells (red).

Figure 17:
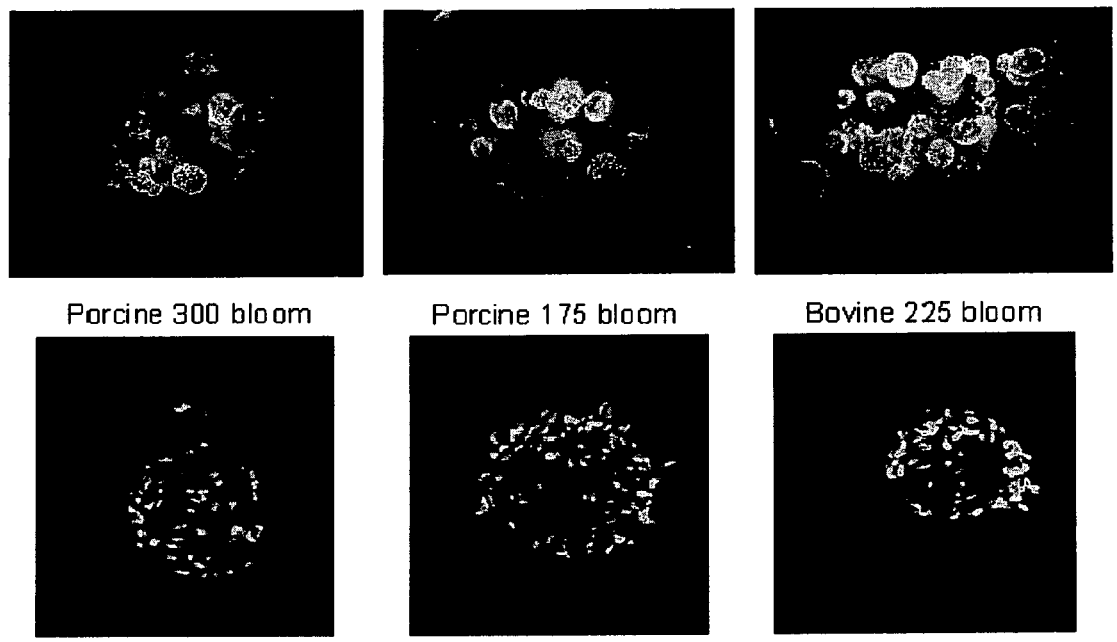

FIG. 17 demonstrates viability of cells (human chondrocytes) after 24 hrs entrapped within various photo-activated cross-linked gelatins. Human chondrocytic cells were pre-seeded onto Cultispher S beads. After growth for days, an aliquot of cells on beads was mixed with gelatin from porcine and bovine origin with different bloom strengths as shown. Photo-activated agents were added and gelatin solutions with cells on beads were cross-linked. After 24 hrs, cell viability was assessed using calcein AM for live cells (green) and ethidium homodimer for dead cells (red). Top row shows low power images of viable cell/beads distribution with the cured gelatin plugs. Bottom rows show higher power confocal images visualising live cells attached on beads within a dark gelatin matrix background.

Figure 18:
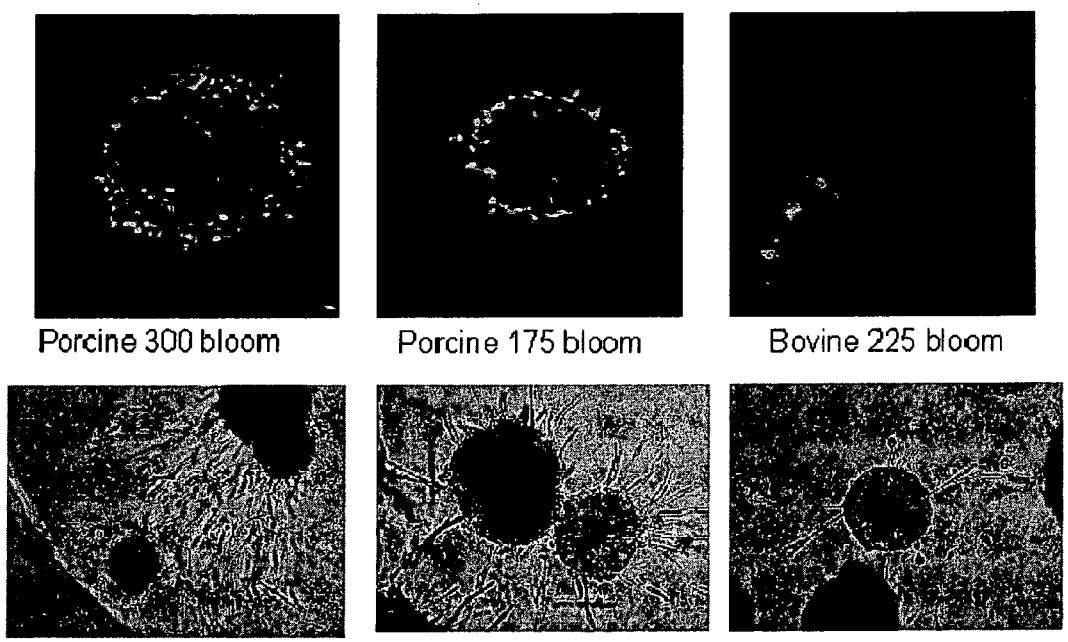

FIG. 18 demonstrates cell migration within the photo-activated cross-linked gelatin matrix. Human chondrocytes were prepared, mixed with porcine gelatin and cross-linked as in FIG. 17. Cell migration was assessed day 1 to day using normal transmission microscopy as well as using fluorescence staining of viable cells as indicated in FIG. 11.

Figure 19:
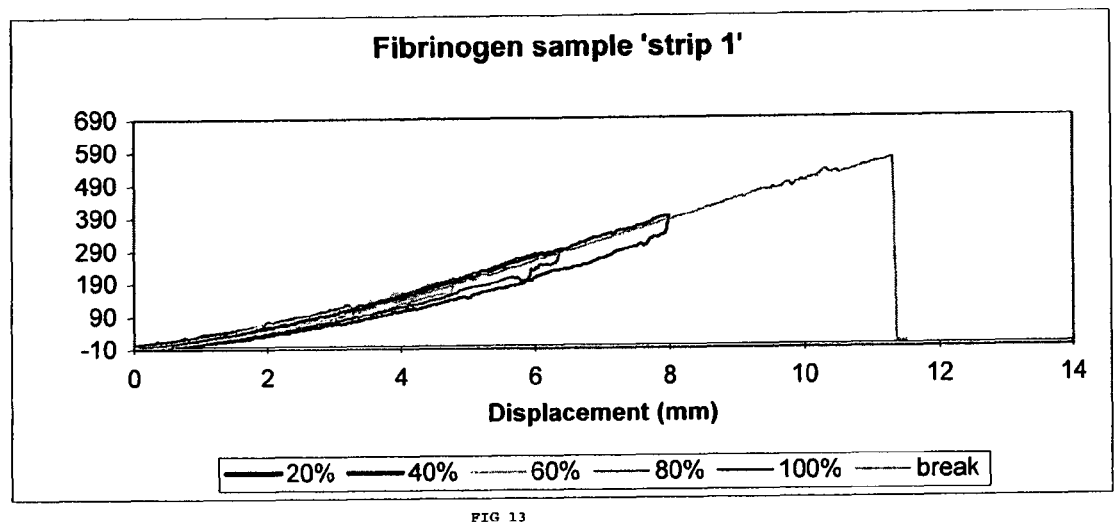

FIG. 19 shows graphically the mechanical properties of photo cross-linked fibrinogen hydrogel. A solution of fibrinogen (150 mg/ml) was prepared in phosphate-buffered saline and ruthenium trisbipyridyl and sodium persulphate were added at 2 mM and 20 mM final concentrations, respectively. A dumbbell-shaped strip (30 mm×4 mm×1 mm) with stainless-steel strips at each end was mounted in the tensile tester and extension increased by steps of 20% strain until the strip failed.

Figure 20:
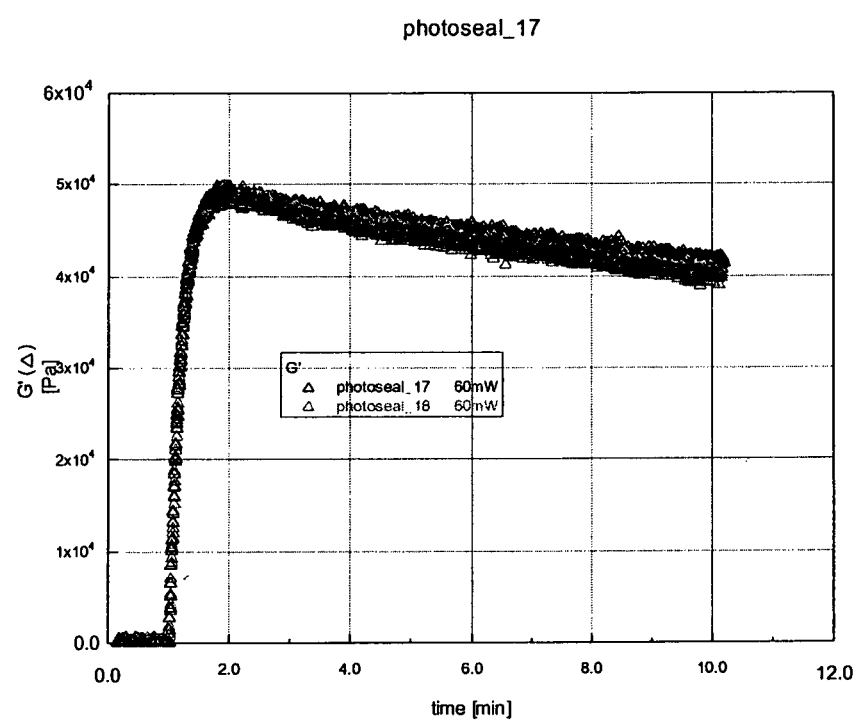

FIG. 20 shows graphically data generated using a Photo-rheometer with a tunable light source and a 400 nm-500 nm filter. The data shows the shear modulus (G')before and after turning on the light (at 1 min) measuring a solution containing 150 mg/ml fibrinogen, 2 mM Ru(II)(bpy)$_3^{2+}$ and 20 mM sodium persulfate in PBS. The reaction is complete within 1 min. Light intensity was 21 mW/cm$^2$. Shear modulus reaches 50 KPa. Duplicate plots overlayed; 3 data points/sec were sampled.

Figure 21:
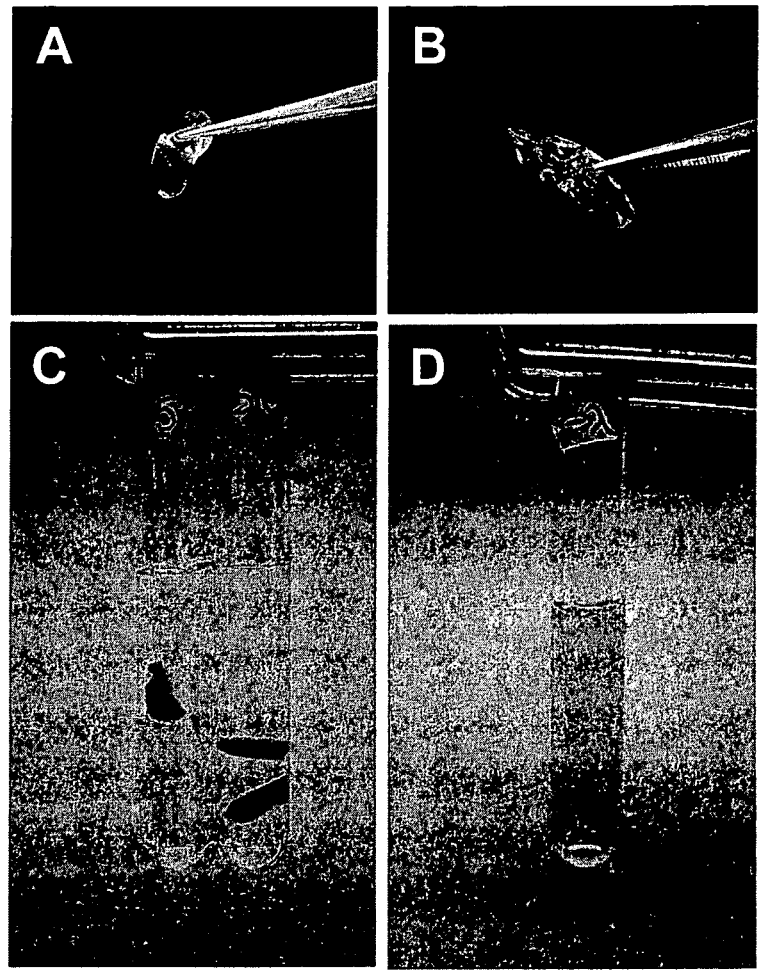

FIG. 21 shows the result of treating two concentrations of fibrinogen for 2 minutes at room temperature with thrombin. Panel A shows a clot formed from a 5 mg/ml solution of fibrinogen (similar to the concentration of fibrinogen in blood—ref: Weisel J W. Fibrinogen and fibrin. Adv Protein Chem. 2005; 70:247-99.). Panel B shows a stiffer clot formed from a 50 mg/ml solution of fibrinogen. Both fibrinogen solutions were treated with 10.5 U of thrombin at room temperature. Both clots were completely soluble in 2.5% acetic acid within 2 minutes at room temperature. Panel C shows photochemically crosslinked fibrin (samples treated as in A, but 2 mM ruthenium tris-bipyridyl and 20 mM sodium persulphate added simultaneously with thrombin in the dark). The samples were then illuminated with white light (600 W tungsten halide lamp) for 10 seconds. Samples were subsequently soaked in 2.5% acetic acid ("5" is fibrinogen at 5 mg/ml; "50" is fibrinogen at 50 mg/ml) and were insoluble as shown. Panel D shows a fibrinogen sample 5 mg/ml) treated with 2 mM ruthenium tris-bipyridyl and 20 mM sodium persulphate, added simultaneously with thrombin in the dark. The fibrin clot was subsequently transferred in the dark to a solution of 2.5% acetic acid. After 2 minutes at room temperature, the clot dissolved completely, demonstrating that, without illumination, no covalent crosslinking occurred in the fibrin clot.

Figure 22:
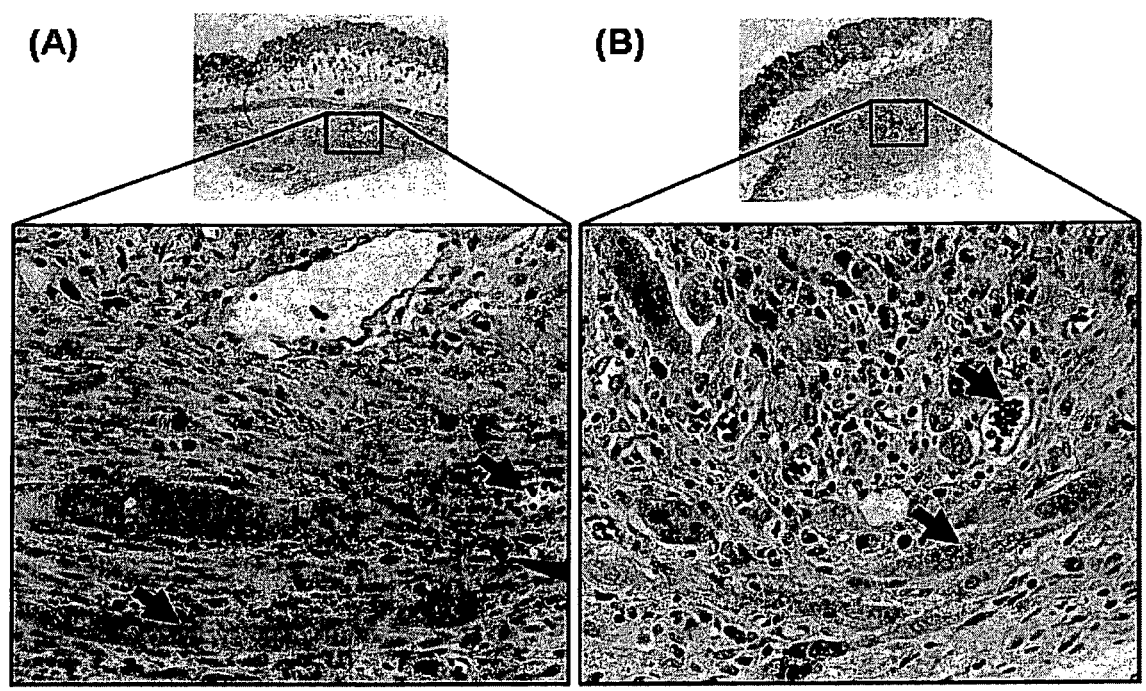

FIG. 22 is a photograph showing foamed, photo-crosslinked fibrinogen scaffolds, seeded with C2 C12 cells and implanted subcutaneously into nude mice. Scaffolds and surrounding tissue were sectioned and stained with Masson's trichrome at 2 weeks (A) and 4 weeks (B) after implantation. Arrows indicate multinucleated myotubes and blood vessels.

DETAILED DESCRIPTION OF THE INVENTION

In one form the invention relates to the preparation of manufactured articles. In an embodiment there is provided a method of manufacturing an article, comprising the steps of:

(1) providing a preferentially associating protein solution, a photoactivatable metal-ligand complex and an electron acceptor;

(2) irradiating the protein solution to photactivate the photoactivatable metal-ligand complex, thereby initiating a cross-linking reaction to form a 3-dimensional matrix of the protein.

In an embodiment the manufactured article is selected from moulded articles such as dressings and pads, implants, lens, tubes, beads and fibres, sponges and sheets.

In an embodiment the manufactured article is a scaffold for tissue engineering or cell-based therapies.

Alternatively the manufactured article may be a scaffold for use in non medical applications such as cell culture or water retention beads.

Thus an embodiment relates to a method of preparing a scaffold for tissue engineering or cell-based therapies, comprising the steps of:

(1) providing a preferentially associating protein solution, a photoactivatable metal-ligand complex and an electron acceptor;

(2) irradiating the protein solution to photactivate the photoactivatable metal-ligand complex, thereby initiating a cross-linking reaction to form a 3-dimensional matrix of the protein.

In an embodiment the protein solution is introduced to a shaped vessel capable of transmitting light so as to allow shaped articles to be produced. Alternatively the solution may be irradiated without a guide to shape the article, and the product will be formed as fibres or beads. Additionally the solution may be sprayed or printed.

In an embodiment the irradiation is conducted prior to implantation of the scaffold or prior to use of the scaffold. However the irradiation may be carried out in full or in part following introduction of the protein solution, be that following partial cross-linking or otherwise, to a patient. Advantageously the protein solution is partially cross-linked to facilitate shaping, and typically is in the form of a hydrogel when introduced to the patient. In an embodiment the hydrogel is injectable.

In a further embodiment there is provided a manufactured article comprising a 3-dimensional matrix of a protein which is capable of preferential association through the interaction of hydrophobic amino acid side chains, wherein said 3-dimensional matrix comprises said protein cross linked by covalent bonds formed between amino acid side chains juxtaposed through the interaction of hydrophobic amino acid side chains of the protein.

In a still further embodiment there is provided a scaffold for tissue engineering comprising a 3-dimensional matrix of a protein which is capable of preferential association through the interaction of hydrophobic amino acid side chains, wherein said 3-dimensional matrix comprises said protein cross linked by covalent bonds formed between amino acid side chains juxtaposed through the interaction of hydrophobic amino acid side chains of the protein.

In an embodiment the protein is a matrix protein. In particular the protein may be selected from, but not limited to the group consisting of fibrinogen, fibrin, collagen, keratin, gelatin, fibronectin, and laminin, or admixtures thereof.

In an embodiment the protein is a globular protein in which preferential association has been induced by chemical modification or unfolding. Unfolding of a protein may be induced by raising or lowering the pH, decreasing or increasing the ionic strength of a protein solution or in other ways know to the person skilled in the art. For example, at pH 4.0 serum albumin is transformed from the "normal" (N) configuration to the "fast (F) configuration. Chemical modification may include addition of attached residues such as tyrosine residues under mild conditions with Bolton-Hunter reagent.

In an embodiment the article is in the form of a hydrogel and such a hydrogel is particularly useful for applications such contact lens, breast implants, reservoirs for drug delivery systems, protective layers on stents and implants so as to provide, for example, absorption, desloughing and debriding capacities of necrotics and fibrotic tissue and for use as a scaffold for tissue engineering or in cell delivery. The article could also be useful in agricultural applications such as a slow release fertilising bead.

In an embodiment the vessel is a transparent mould adapted to produce a shaped article. This may be of tubular design, for example for introduction as part of a lumen of a blood vessel, duct or tract such as the urinary tract. Alternatively the shaped article may be a prosthesis shaped to fit a particular surface, a sheet or mat, a membrane or a sponge.

In an embodiment the protein is introduced into a tissue or tissue defect and irradiated in situ to photoactivate the photoactivatable metal-ligand complex. The product may be introduced directly without concern for the shape. For example, a protein solution may be prepared with live cells as inclusions and cured in situ before, during or after injection.

In an embodiment the protein solution further comprises a therapeutic agent selected from the group consisting of cells, growth factors, bioactive agents and nutrients. In an embodiment a drug (particularly a chemotactic, growth promoting or differentiation factor but also a conventional drug such as an antibiotic or chemotherapeutic drug) is introduced to the protein solution. While not wishing to be bound by theory it is believed that the therapeutic agent is captured in the 3-dimensional matrix formed by the cross-linking reaction and so retained in situ for an extended period before the matrix degrades.

Additionally, the present inventors have found that the photochemical reaction described herein can create covalent cross-links between endogenous proteins if applied to a tissue. Thus in an embodiment there is envisaged a method of joining and/or sealing tissues in a surgical procedure or medical treatment, comprising the steps of:

(1) applying a photoactivatable metal-ligand complex and an electron acceptor to a tissue portion;

(2) irradiating said tissue portion to photoactivate the photoactivatable metal-ligand complex;

thereby initiating a cross-linking reaction between one or more endogenous matrix proteins to seal said tissue portion or join said tissue portion to an adjacent tissue portion.

In particular, the photochemical reaction described herein can form covalent crosslinks in a fibrin matrix such as that formed when thrombin catalyses the conversion of fibrinogen into fibrin in haemostasis. Thus it may be used to enhance the adhesive strength of the clot formed when haemostasis takes place in vivo.

In an embodiment thrombin is applied to the tissue whereby fibrin is formed by cleavage of endogenous fibrinogen under the influence of the applied thrombin and said fibrin is involved in the photoactivated cross-linking reaction. It will also be appreciated that a combination of prothrombin and calcium applied to a wound site can also serve as a source of thrombin.

The method may involve moving the said tissue portion to a position adjacent, inclusive of touching, the adjacent tissue portion, where necessary, such as when a relatively large gap exists between them. Alternatively, the matrix resulting from the cross-linking reaction may form a plug which nevertheless binds the tissues to either side of an incision or opening. Furthermore, the cross-linked matrix may form a coating over a region of tissue, and may be shaped or supported as appropriate, for example, the thrombin and/or photoactivatable metal-ligand complex and electron acceptor may be carried by a collagen sheet or impregnated in a surgical gauze or fleece. Accordingly, it will be appreciated that the cross-linked matrix can adopt a physical form to suit the application in which it is used, and it will be applied in the appropriate manner to suit that purpose.

In an embodiment the method is used to seal a vessel. This may be to seal blood vessels to prevent blood loss, to treat lung tissue for sealing air leaks, to prevent cerebrospinal fluid leakages or to seal a vessel to prevent leakage of any other biological fluid.

In an embodiment the method is used to join a first tissue portion and a second tissue portion to seal a wound such as an incision, for example, in aesthetic or cranial surgery.

In an embodiment the method is used to treat a soft tissue such as liver or lung tissue which has suffered injury, for example, by coating the tissues.

Tissue adhesives of the present invention may also be used as wound dressings, for example, if applied alone or in combination with adhesive bandages, or as a haemostatic dressing in the operating room.

In an embodiment there is provided a closure for a leaking wound comprising a substrate suitable for application to a wound to stem leakage, wherein said substrate is impregnated or coated with a photoactivatable metal-ligand complex and an electron acceptor.

In an embodiment the closure further comprises thrombin.

In an embodiment the substrate is a bandage, gauze, cloth, tampon, membrane or sponge.

In this embodiment there is also envisaged a method of stemming bleeding from a wound comprising applying a closure as described to the wound and irradiating the closure and surrounding tissue, thereby causing a cross-linking reaction between fibrin formed by cleavage of endogenous fibrinogen under the influence of the thrombin within or coating the closure and one or more endogenous matrix proteins in the surrounding tissue to join the closure to the surrounding tissue.

According to a further aspect of the present invention there is provided a kit comprising a thrombin, a photoactivatable metal-ligand complex and an electron acceptor.

In an embodiment the thrombin, metal-ligand complex and an electron acceptor are separately contained within the kit.

The kit optionally contains buffer, such as phosphate buffered saline, for preparation of solutions of one or more thrombin, photoactivable metal-ligand complex and electron acceptor. The kit may include a weak acid such as acetic acid to render an otherwise insoluble matrix protein such as fibrin soluble.

A light source may also be provided in the kit, particularly where the kit is for use in the field.

In an embodiment a wound closure such as a bandage, gauze, cloth, tampon, membrane or sponge may be provided in the kit and, optionally, may be pre-impregnated or pre-coated with thrombin, a photoactivable metal-ligand complex and an electron acceptor.

In an embodiment, a composition comprises one or more of thrombin, a photoactivatable metal-ligand complex and an electron acceptor and inert carrier. In particular, these compounds are dissolved in an inert carrier, and a solution comprising all three components is applied to the tissue portion. In particular, the solution is an aqueous solution, and generally a solution in a buffer such as phosphate buffered saline. Alternatively, each of the three components could be applied separately, or as separate solutions, prior to irradiation.

The method of application is not critical and may involve spreading of a solution over the appropriate tissues or over a region to be sealed or rubbing of one tissue portion on another to spread the solution.

In an embodiment the thrombin composition further comprises human blood factor XIII. Factor XIII is a compound that strengthens blood clots by forming covalent cross-links between strands of fibrin.

In an embodiment the thrombin composition further comprises aprotinin and factor XIII. Aprotinin is a protein that inhibits the enzymes that break down blood clots.

In an embodiment a drug (particularly a chemotactic, growth promoting or differentiation factor but also a conventional drug such as an antibiotic or chemotherapeutic drug) or other therapeutic agent is applied to said first tissue portion and/or said second tissue portion, in particular, as a component of the composition described above. While not wishing to be bound by theory it is believed that the therapeutic agent is captured in the matrix formed by the cross-linking reaction and so retained in situ for an extended period before the matrix degrades.

In another embodiment, there is envisaged a method of joining and/or sealing at least one substrate, comprising the steps of:

(1) applying a protein or peptide solution, a photoactivatable metal-ligand complex and an electron acceptor to at least one substrate;

(2) irradiating said material to photactivate the photoactivatable metal-ligand complex;

thereby initiating a cross-linking reaction to adhere or join said substrate to an adjacent substrate.

In one embodiment the protein may be a partially denatured protein such as serum albumin or gelatin or alternatively a matrix protein such as fibrinogen or collagen.

In an embodiment the protein is applied to a surface of one or more items to be joined or sealed and irradiated in situ to photoactivate the photoactivatable metal-ligand complex to adhere one item to another or seal the surface of one or more items. Thus the protein may be used as an adhesive or a sealant and photoactivated to form the adhesive link or make the seal. The person skilled in the art will appreciate that numerous items may be joined or sealed in this way including items manufactured from glass, metal, wood, thermoplastic or thermosetting polymeric materials, and so on. The use as an adhesive or sealant may involve the connection or sealing of items without restriction as to form, and includes household items, timber products and manufactured goods. Thus it is envisaged that the sealant may be used as an adhesive in non medical applications such as in joining wood products in mending underwater pipes, in labelling of bottles. These crosslinked materials provide a non toxic, strong alternative adhesive to the currently used adhesives.

The present inventors have made the unexpected observation that self-association can be induced and/or enhanced via total or partial denaturation of a peptide or protein or by chemical modification which renders proteins previously in the native state susceptible to photochemical cross linking.

In an embodiment there is provided a method of joining and/or sealing materials in a surgical procedure, medical treatment, comprising the steps of:

(1) applying an at least partially denatured protein, a photoactivatable metal-ligand complex and an electron acceptor to a substrate;

(2) irradiating said substrate to photoactivate the photoactivatable metal-ligand complex;

thereby initiating a cross-linking reaction to form a matrix comprising said at least partially denatured protein to seal or join said substrate to an adjacent substrate;

wherein said at least partially denatured protein has been rendered more susceptible to cross-linking compared to its native state.

In a preferred embodiment said substrate is a tissue portion.

In an embodiment said at least partially denatured protein is an at least partially denatured matrix protein and said matrix protein is selected from the group consisting of fibrinogen, fibrin, collagen, fibronectin, keratin and laminin, or admixtures thereof.

In an embodiment denaturation occurs by heating.

In an alternative embodiment said at least partially denatured protein is a globular protein in which preferential association has been induced by chemical modification or unfolding. Unfolding of a protein may be induced by raising or lowering the pH, decreasing or increasing the ionic strength of the solution, or in other ways, known to a person skilled in the art.

In an embodiment physical or mechanical denaturation techniques are employed. Typically a mechanical force such as stirring or agitation of a protein solution is used to produce a "foam". This may find particular application where a space filling sealant or adhesive is desirable. Alternatively compressed gas could be introduced to the protein solution to achieve denaturation and to facilitate delivery of the sealant.

In an embodiment denaturation occurs by way of acid/alkali treatment or pH adjustment.

In an embodiment said at least partially denatured protein is gelatin. Gelatin is produced by the partial hydrolysis of collagen, which causes the natural molecular bonds between individual collagen strands to be broken down into a denatured form. Typically hydrolysis occurs by lowering the pH.

In an embodiment said at least partially denatured protein is serum albumin in which the "fast" (F) configuration has been induced. Typically the F configuration is induced by reduction of the pH to 4.0 and occurs through dissolution of serum albumin in a weakly acidic solution or by addition of a weak acid to an aqueous solution. The N to F transition involves the unfolding of domain III, with an increase in viscosity, much lower solubility and a decreased helical content. While not wishing to be bound by theory, it is believed that this transition reveals hydrophobic residues which would otherwise have been located internally in this (in the N configuration) globular protein and so serum albumin self associates when in the F configuration at pH 4.0.

In an embodiment chemical modification is employed to render susceptible the protein to cross-linking compared to its native state. Such chemical modification may include the modification of amino acid side chains to include of aromatic moieties such as the phenolic moiety present in tyrosine. By way of example primary amines such as the lysine residues in a protein may be modified under mild conditions with Bolton-Hunter reagent (N-succinimidyl-3-[4-hydroxyphenyl]propionate) or water soluble Bolton-Hunter reagent (sulfosuccinimidyl-3-[4-hydroxyphenyl]propionate). Equally it may involve modification of the protein to alter its secondary, tertiary or quaternary structure. Protein modification agents are well known to the person skilled in the art and include reagents which can effect sulfhydryl reduction, addition of sulfhydryl or amino groups, protein acylation, etc.

Tissue adhesives of the present invention may also be used as wound dressings, for example, if applied alone or in combination with adhesive bandages, or as a hemostatic dressing in the operating room. Adhesives of the present invention may also be used in non-medical applications such as in pipe repair, labelling of bottles, as well as in general adhesive and sealing applications.

Accordingly, an embodiment provides a closure for a bleeding wound comprising a substrate suitable for application to a wound to stem bleeding, wherein said substrate is impregnated or coated with an at least partially denatured protein, a photoactivatable metal-ligand complex and an electron acceptor, wherein said at least partially denatured protein or chemically modified protein is rendered more susceptible to photochemical cross-linking compared to its native state.

In an embodiment the substrate is a bandage, gauze, cloth, tampon, membrane or sponge.

Additionally this embodiment provides a method of stemming bleeding from a wound comprising applying a closure as described to the wound and irradiating the closure and surrounding tissue.

In a further embodiment there is provided a composition comprising an at least partially denatured protein, a photoactivatable metal-ligand complex and an electron acceptor, wherein said at least partially denatured protein or chemically modified protein is rendered susceptible to photochemical cross-linking compared to its native state or susceptibility to photochemical cross-linking is enhanced.

A further embodiment provides a kit comprising an at least partially denatured protein, a photoactivatable metal-ligand complex and an electron acceptor, wherein said at least partially denatured protein or chemically modified protein is rendered more susceptible to photochemical cross-linking compared to its native state.

In an embodiment the at least partially denatured protein, metal-ligand complex and an electron acceptor are separately contained within the kit.

The kit optionally contains buffer, such as phosphate buffered saline, for preparation of solutions of one or more of the denatured protein, photoactivable metal-ligand complex and electron acceptor. The kit may include a weak acid such as acetic acid to allow for in situ denaturation.

A light source may also be provided in the kit, particularly where the kit is for use in the field.

In an embodiment a wound closure such as a bandage, gauze, cloth, tampon, membrane or sponge may be provided in the kit and, optionally, may be pre-impregnated or pre-coated with an at least partially denatured protein, a photoactivable metal-ligand complex and an electron acceptor.

In an embodiment, a composition comprises one or more of an at least partially denatured protein, a photoactivatable metal-ligand complex and an electron acceptor and inert carrier. In particular, these compounds are dissolved in an inert carrier, and a solution comprising all three components is applied to the tissue portion. In particular, the solution is an aqueous solution, and generally a solution in a buffer such as phosphate buffered saline. Alternatively, each of the three components could be applied separately, or as separate solutions, prior to irradiation.

In an embodiment a drug (particularly a chemotactic, growth promoting or differentiation factor but also a conventional drug such as an antibiotic or chemotherapeutic drug) or other therapeutic agent is applied to said first tissue portion and/or said second tissue portion, in particular, as a component of the composition described above. While not wishing to be bound by theory it is believed that the therapeutic agent is captured in the matrix formed by the cross-linking reaction and so retained in situ for an extended period before the matrix degrades.

MODES FOR PERFORMING THE INVENTION

At least in preferred embodiments the invention provides a rapid, specific and biocompatible process for covalent cross-linking of selected proteins (soluble and/or insoluble), including ECM proteins. The articles which result may be used in contact lens, sheet dressings of wound dressings or pads, as breast implants, as cartilage implants, as a component in nerve sheaths and novel blood vessel constructs, as components in water retention applications or 3 dimensional cell culture matrices or in orthopaedic applications.

The materials are porous and potentially resorbable and so particularly useful as scaffolds that can be used directly as injectable hydrogels or engineered into structures for e.g. delivery of cells; reconstruction of soft tissues/organs including skin; directed migration and population by endogenous cells; delivery or augmentation of enzymes/growth factors etc; also cross-linking or treatment of acellular or naturally derived tissues/organs; also scaffolds for culturing cells. Additionally control can be exerted over the biomechanical properties of the materials by various means e.g. composition of the protein matrices and regulation of degree of cross-linking. Advantageously, bonding of the matrices/scaffolds to endogenous ECM at the site of application is believed to take place. Furthermore, degradation/resorption rates can be varied by controlling the parameters outlined above.

The present inventors have found a means of preparing tissue scaffolds and matrices using soluble ECM components or other molecules which preferentially associate and form covalently linked, high-molecular weight hydrogels using a novel, cell-compatible process. The process can be used to construct stable, proteinaceous scaffolds for the delivery of cells or for organ and tissue reconstruction as well as matrices suitable e.g. for burns and open wound treatment, soft tissue implants and cell culturing.

The cross linking imparts a mechanical stability and degradation control that is lacking in the current materials. Another major advantage of this system is the controllable and rapid gelation of preferentially associating protein or peptide solutions, which allows in-situ curing to be carried out. Injectable gels as well as prostheses can be formulated and cured to form a biocompatible, covalently cross-linked network with mechanical properties matched to the surrounding tissue or ECM. The porous structure and protein composition of cross-linked polymer matrices promotes tissue regrowth and the rate of degradation can be tailored to complement the rate of tissue repair. Because the cross-linking process is essentially biocompatible the system can be used as a delivery vehicle for cells, growth factors, bioactive agents and nutrients. Thus the physical, mechanical and biological characteristics can be tailored to specific needs both in medical and non medical applications.

The present inventors have recognised that the natural strong preferential association of peptides or proteins would likely result in the inter- and intra-molecular conjunction of a number of individual aromatic amino acid residues such as tyrosine and histidine, most particularly, tyrosine residues. They have inferred that this would render preferentially associated proteins susceptible to covalent bonding and polymerisation using a photoactivatable catalyst capable of inducing formation of a stabilised free radical on adjacent side-chains so as to initiate formation of a carbon-bond between the two. Consequently they have successfully cross-linked proteins in a photo-initiated chemical process in which a metal-ligand complex in conjunction with an electron acceptor directly mediates cross-linking between adjacent proteins through a mechanism which does not involve formation of potentially detrimental species such as singlet oxygen, superoxide or hydroxyl radicals. While not wishing to be bound by theory, it is believed that the mechanism involves irradiation of the metal-ligand complex to induce an excited state, followed by transfer of an electron from the metal to an electron acceptor. The oxidised metal then extracts an electron from a side chain such as a tyrosine side chain in the protein to produce, a tyrosyl radical which reacts immediately with a nearby tyrosine to form a dityrosine bond. A direct cross-link (without any bridging moiety) is created quickly in this photo-initiated chemical reaction, without the need for introduction of a primer layer and without the generation of potentially detrimental species such as singlet oxygen, superoxide and hydroxyl radicals.

The term "photoactivatable metal-ligand complex" as used herein means a metal-ligand complex in which the metal can enter an excited state when irradiated such that it can donate an electron to an electron acceptor in order to move to a higher oxidation state and thereafter extract an electron from a side chain of an amino acid residue of a matrix protein to produce a free radical without reliance upon the formation of singlet oxygen. Suitable metals include but are not limited to Ru(II), Pd(II), Cu (II), Ni(II), Mn (II) and Fe (III) in the form of a complex which can absorb light in the visible region, for example, an Ru(II) bipyridyl complex, a Pd(II) porphyrin complex, a sulfonatophenyl Mn(II) complex or a Fe(III) protoporphyrin complex, more particularly, an Ru(II) bispyridyl complex or a Pd(II) porphyrin, in particular, an Ru(II)(bpy)$_3$ complex such as [Ru(II)(bpy)$_3$]Cl$_2$. Efficient cross-linking occurs in the presence of an electron acceptor, and requires only moderate intensity visible light. The options and types of chemistry involved are outlined in Brown et al (2001) the contents of which are incorporated herein by reference.

As used herein the term "electron acceptor" refers to a chemical entity that accepts electron transferred to it and so refers to an easily reduced molecule (or oxidizing agent) with a redox potential sufficiently positive to facilitate the cross-linking reaction. A range of electron acceptors will be suitable. In an embodiment the electron acceptor the electron acceptor is a peracid, a cobalt complex, a cerium (IV) complex or an organic acid. Typically the electron acceptor is a persulfate, periodate, perbromate or perchlorate compound, vitamin B12, Co(III)(NH$_3$)$_5$Cl$^{2+}$, cerium(IV)sulphate dehydrate, ammonium cerium(IV) nitrate, oxalic acid or EDTA.

Preferably the persulfate anion is used as the electron acceptor, as it is one of the strongest oxidants available. The standard oxidation reduction potential for the reaction

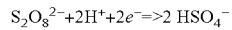

is 2.1 V, as compared to 1.8 V for hydrogen peroxide (H2O2). This potential is higher than the redox potential for the permanganate anion (MnO$_4^-$) at 1.7 V, but slightly lower than that of ozone at 2.2 V.

As used herein the term "matrix protein" refers to isolated and purified forms of the proteins which are abundant and common in the extracellular matrix of animals. Typical matrix proteins are fibrinogen, fibrin, collagen, fibronectin, keratin, laminin, elastin; or admixtures thereof, and these may be isolated from human or animal sources or prepared, for example, using recombinant DNA technology. As well, the inventors have observed that the preferentially associating proteins beta-lactoglobulin; gelatin; glycinin; glutens; gliadins and resilin can be rendered into hydrogels using the process described herein, and may find application in particular embodiments of the invention. In addition, derivatives of these compounds, including peptide derivatives or extracts containing them are suitable for use in the present invention, and they may be used in admixture. Furthermore they may be present as native proteins or may be denatured and, provided preferential association will take place, present under a range of conditions such as high or low pH, high or low salt concentrations and in aqueous or non-aqueous solution.

As herein the term "protein solution" refers to a solution or dispersion of one or more peptides or proteins in a solvent or a solvent mixture. Typically the solution is an aqueous solution and may include a co-solvent such as ethanol, and may be a buffer solution. The term includes a dispersion of hydrated protein or denatured protein granules. The protein solution may comprise a single peptide or protein or a mixture of peptides or proteins having the property of self association, whether these be peptides or proteins that preferentially associate in their natural state or not, as peptides or proteins which possess the inherent property of self association but do not occur together or do not preferentially associate in nature may nevertheless associate when in admixture in solution.

As used herein the term "aromatic amino acid" refers to an α-amino acid in which the side chain comprises a substituted or unsubstituted aryl or heteroaryl group. The 20 or so common, naturally-occurring amino acids include the aromatic amino acids phenylalanine, tyrosine and tryptophan and histidine.

As used herein the terms "fibrin" and "fibrinogen" encompass fibrin and fibrinogen themselves, purified fibrin or fibrinogen sub-units or composites or admixtures thereof. These might be isolated from human or animal whole blood or plasma. Alternatively these products or active homologs or fragments thereof may be prepared by genetic engineering, and such products are also envisaged for use in the present invention. For example, Pharming is developing three fibrinogen genes (rTS) under the transcriptional control of the bovine α-S1 casein promoter to achieve high level, mammary gland-specific expression. Nuclear transfer technology has been used to generate a number of transgenic cows that show expression levels of human fibrinogen in the milk at levels of 1-3 g/l.

The inventors have also demonstrated that clotted fibrin itself (produced by treatment of soluble fibrinogen with thrombin and insoluble in phosphate buffer) can be rendered soluble by, e.g. addition of 2% acetic acid or other means, and this can also subsequently be cross-linked using the method of the invention.

As used herein the term "soluble fibrin" refers to fibrin that has been prepared from fibrinogen by, for example, hydrolysis with thrombin, then rendered soluble by addition of a weak acid such as 2% acetic acid, a chemical chaotrope such as urea, or other means.

As used herein the term "applying" or "apply" or "application" refers to sequential application of the matrix protein, photoactivatable metal-ligand complex and the electron acceptor in any order or to application of compositions comprising any one or more of the matrix protein, photoactivatable metal-ligand complex and the electron acceptor. The matrix protein, photoactivatable metal-ligand complex and the electron acceptor or compositions containing them in admixture may be provided in solid form such as a lyophilized powder or a plug of material or in liquid such as a solution or foam.

As used herein the term "self associate" or its equivalents "self associates", "self associating", "self association" and the like, refer to the inherent property of a protein to associate with itself through hydrophobic interaction or bonding i.e. through the association of non-polar groups or domains in aqueous media due to the tendency of water molecules to exclude non-polar species. Salt bridges can also commonly occur to facilitate and stabilize protein and peptide interactions. The matrix proteins typically self associate in their natural configuration in aqueous media. It will be appreciated additionally that self association can be induced by altering the natural configuration, for example by inducing some unfolding of a protein such as by altering the pH or ionic strength of the media. For example, at pH 4.0 bovine serum albumin is transformed from its normal (N) configuration to the so-called "fast" (F) configuration, and the N to F transition involves the unfolding of domain III, with an increase in viscosity, much lower solubility and a decreased helical content. While not wishing to be bound by theory, it is believed that this transition reveals hydrophobic residues which would otherwise have been located internally in this (in the N configuration) globular protein and so it self associates when in the F configuration at pH 4.0.

As herein the term "preferentially associate" "preferentially associate" or its equivalents "preferentially associates", "preferentially associating", "preferentially association" and the like refers to peptides and proteins that have the inherent characteristic of self-association but which, if brought into juxtaposition with another protein having this characteristic will associate with it. Therefore a self associating protein is, in effect, a preferentially associating protein. Additionally, the term refers to peptides and proteins that have specific interaction domains through which they interact and associate through hydrophobic interaction or bonding i.e. through the association of non-polar groups or domains in aqueous media due to the tendency of water molecules to exclude non-polar species. Salt bridges can also commonly occur to facilitate and stabilize protein and peptide interactions. By way of example collagen and fibronectin and fibrinogen and fibronectin possess domains which preferentially bind to each other so that naturally self associate.

As used herein the term "tissue" refers to a plurality of cells located in close juxtaposition, be they alike in character or unlike, and so includes a tissue in the histological sense such as muscle tissue but also includes discrete structures such as the walls of a vessel like a blood vessel and the surface of an organ, including a raw, cut surface. The usage of the term should be read in conjunction with the intended uses described herein, and is not intended to limit the uses described.

As used herein the term biomaterial refers to an article that has been made from proteinous or peptide material and that is preferentially for medical use, such as for use as an implant, as a tissue sealant or as a tissue scaffold. In the alternative the biomaterial could be used for non-medical use as described herein. It will be appreciated that the biocompatibility of such materials is not necessarily advantageous, as it is in medical use, but non-medical applications are not excluded for this reason solely.

Composite materials may be used to regulate the bulk properties of the biomaterial (stiffness, elasticity or modulus) so that the hydrogel thus formed has bulking or filling properties suitable for tissue implants or prostheses that may be naturally bonded to surrounding tissues. Suitable materials might include mineral, metal or inorganic inclusions (e.g. hydroxyapatite or nanocrystalline titanium or other metal salts), synthetic organic compounds (plastics or other polymers) or natural organic polymers (e.g. chitin, chitosan or cellulosic materials).

In an embodiment the protein is present in a solution or solution mixture, typically a solution with a protein concentration in the range of 0.1-20% w/v, preferably 0.5-10% and most often 0.5-2% or more for collagen; typically 5% or more for other proteins, e.g. fibrinogen. The person skilled in the art will appreciate that solutions with a higher concentration of protein may be effectively cross-linked but economic considerations dictate that very high concentrations of protein will not be used, and that there is a limit to the concentration of protein which will remain in solution. Likewise, solutions with a lesser concentration of protein may be cross-linked although the gel resulting from this procedure may be less effective.

In an embodiment an appropriate concentration of single protein solution (typically 0.5-2% or more for collagen; typically 5% or more for other proteins, e.g. fibrinogen) or composites of suitable proteins in solvent, solvent mixture or buffer is mixed with 2 mM $Ru(Bpy)_3$ and 20 mM persulphate salt (sodium, ammonium, potassium etc) and irradiated with white light (450 nm nominal wavelength) for at least 10 secs. to form the hydrogel. This process is cell compatible. To form 3-dimensional structures the biomaterial can be cast or contained within transparent moulds. If performed in situ the process will covalently link the hydrogel thus formed with surrounding tissues with a natural affinity (e.g. those containing integrins) thereby forming an endogenous bond.

To determine the effect of cross-links and the optimal number of cross-links per monomer unit, the resilience of a cross-linked protein can be measured using methods known in the art. The level of cross-linking can vary. For example, the degree of cross-linking is a function of the time and energy of the irradiation. The time required to achieve a desired level of cross-linking may readily be computed by exposing non-cross-linked polymer to the source of radiation for different time intervals and judging the suitability of the resulting cross-linked material for each time interval. By this experimentation, it will be possible to determine the irradiation time required to produce an appropriate material for a particular application (see, e.g., U.S. Pat. No. 4,474,851, the contents of which are incorporated herein by reference).

The ability to tune the cross-linking by changing the irradiation conditions renders the resultant biomaterial, manufactured article, sealant or adhesive highly versatile.

The proteins are preferably lightly cross-linked. Preferably, the extent of cross-linking is at least about one cross-link for every five or ten to one hundred monomer units, e.g., one cross-link for every twenty to fifty monomer units. The extent of cross-linking may be monitored during the reaction or pre-determined by using a measured amount of reactants. For example, since the dityrosine cross-link is fluorescent, the fluorescence spectrum of the reactant mixture may be monitored during the course of a reaction to determine the extent of cross-linking at any particular time. This allows for control of the reaction and the properties of the scaffold which results.

The photochemical reaction described above can form covalent crosslinks in a extracellular protein matrix. The inference is that addition of a photoactivatable metal-ligand complex and an electron acceptor to a wound where endogenous extracellular matrix proteins are present or where thrombin is present and induction of a photochemical process, will induce or enhance the clot formation as a haemostatic agent in vivo. While not wishing to be bound by theory, it is believed that the ruthenium complex-mediated protein oxidation carries out a very rapid covalent crosslinking reaction, thereby stabilising the thrombin-derived clot in a manner analogous to the function of Factor XIII-mediated crosslinking (Lee M G and Jones D (2005)).

Therefore in embodiments of the invention addition of a photoactivator such as ruthenium tris-bipyridyl chloride and an electron acceptor such as sodium persulphate (or an equivalent salt) to a solution of thrombin, followed by treatment of, e.g. a tissue or wound site with the composition, then illumination with visible light, would enable covalent crosslinking of the thus-formed fibrin clot. This may also involve crosslinking of the fibrin clot to other components of the extracellular matrix (ECM) and would therefore improve the strength and stability of a thrombin-induced clot for haemostasis. Fibrin is known to interact with a number of ECM proteins (Makogonenko et al (2007)

In further embodiments application of the photoactivator and electron acceptor alone, followed by irradiation, can induce crosslinking of endogenous matrix proteins.

It is envisaged that the method of the present invention will be used to augment or as a replacement for conventional surgical closures such as sutures and staple and existing tissue adhesives generally; however, it is likely to have particular application in certain fields and applications. In particular the method will find application in fields where tissue adhesives such as fibrin glue are already used such as in cardiothoracic surgery, cardiovascular surgery, thoracic surgery, hepatic and pancreatic surgery, neurosurgery, aesthetic surgery, endoscopic surgery, cranial surgery, prevention of seroma formation, bone healing, liver biopsy and dentistry.

The effectiveness of a sealant on hemostatis in cardiothoracic surgery is important to the clinical outcome; successful local hemostatis reduces blood loss, operative time, and the need for resternotomy in these high risk patients. Bleeding after open-heart surgery is a great problem in cardiac surgery. Due to hemostatic abnormalities, reoperation to control prolonged bleeding may be necessary. Therefore a sealant superior at producing hemostatis compared with conventional topical agents, such as collagen-coated dressings is desirable.

The method of the present invention will also be useful for sealing air leaks from lung procedures (even as treatment for bronchopleural fistulas). Thoracic surgery frequently involves pulmonary resection and decortications. The consequences of such surgical intervention include haemorrhage and air leaks. Retrospective analyses indicate that bronchopleural fistulae occur in 2% to 3% of patients after pulmonary resection, followed by a mortality of 15% to 20%. These complications can be overcome by the use of sealants of the invention.

Raw cut surfaces of soft tissues such as liver and lung cannot be isolated and secured by conventional techniques such as suturing. The management of these surfaces is important for preventing intrapertoneal complications, such as infection, abscess formation, and sepsis which may lead to haemorrhage, bile leakage, and fluid accumulation. Moreover, bile fluid is a severe irritant to the peritoneum and the prevention of bile leakage using a fibrin sealant is highly desirable. Therefore the sealant of the present invention finds application as a tissue sealant in hepatobiliary surgery.

Fibrin glue is used for dural closure by neurosurgeons to prevent cerebrospinal fluid leakages. The management of cerebrospinal fluid (CSF) fistulae is important. Fibrin sealant has been used in neurosurgical procedures for the prevention of CSF leakage from fistulae, and the sealant of the present invention will find application in preventing CSF leakages Aesthetic surgeons in Europe have routinely used fibrin-based glues in place of sutures, which has enabled them to avoid the use of drains for patients undergoing facial cosmetic surgery. There are basically two advantages of avoiding the use of drains and dressings: the postsurgical time is reduced by not putting on and removing the usual bulky dressings, and swelling, hematoma formation is reduced. Tissue adhesives have been reported to decrease the incidences of postoperative hematomas and edema, enable painful suture removal to be avoided, and, in some cases, facilitate early recovery and greater patient satisfaction. Plastic surgeons especially use adhesives to control burn bleeding after debridement and as adjuncts in surgery necessitating flaps. Skin grafting is the simplest and most effective method used to resurface large burn wounds. The graft initially adheres to its new bed by a thin layer of fibrin and nourishment of the graft occurs by plasmatic imbibition. Further ingrowth of blood vessels and fibrous tissue from the wound results in permanent adherence of the graft to its recipient site known as graft "take." This process can be hindered by collection of blood between the graft and bed, by shearing and by infection. The face is highly vascular and diffuse bleeding is difficult to control following burn wound excision. Traditionally, to overcome the problem of hematoma, the grafts are meshed to enable any fluid collection to drain. Unfortunately meshing produces scarring which impairs the final cosmetic result. Careful suturing can minimize shearing, but takes time, may promote bleeding and also leaves scars. The sealant of the present invention has several advantages in the excision and skin grafting of facial burns as it provides good hemostasis and helps prevent hematoma formation, it minimizes the use of sutures, which save operating time, and it avoids further bleeding during passing of the sutures. Plastic surgeons are also utilizing fibrin glue for the management of wrinkles of the forehead and of the aging face, and the sealant of the present invention will also be useful in this application. The technique avoids the classic coronal incision, utilized for the browlifting, thus minimizing morbidity. The adhesive not only helps to secure the forehead and scalp flaps in place, but also works as a hemostatic agent, decreasing hematoma formation and bruising.

The collection of serous fluids after operations is a very threatening problem and should be prevented. It can cause significant morbidity and delayed recovery. It can appear after a mastectomy and axillary dissection, soft tissue dissection (abdominoplasty, breast reduction, facelift), and muscle harvesting. The complications include pain, wound infection, flap necrosis, and increased costs but wound healing can be improved with intraoperative sealant application.

Use of the tissue adhesive in bone repair should promote osteoblastic activity rather than retarding it. In contrast, cyanoacrylates cause adverse bone reaction. Their space occupying nature prevents or retards healing and their degradation products are harmful.

Liver biopsy is frequently necessary for candidate evaluation or histologic follow-up of transplanted livers. Although generally considered to be safe, it carries a risk of complications in up to 0.5% of cases; haemorrhage being the most important. Another option is the so-called plugged percutaneous liver biopsy (PPLB), which uses direct injection of a plugging material into the biopsy tract, and sealants of the present invention could be used.

In dentistry the use the use of tissue adhesives shows less propensity for infection or delayed healing compared to the use of silk sutures which can result in foreign body reaction, fistula formation and submental abcess formation.

Tissue adhesives of the present invention may also be used as wound dressings. Absorbable adhesive bandages can be directly used in the control of battlefield wounds, and immediate local control of bleeding can be achieved. A further application may be as a hemostatic dressing in the operating room which is used instead of a sponge.

It is also envisaged that the present invention will provide a vehicle for local administration of drugs. It has the ideal characteristics to play such a role. In the method of the invention the thrombin is placed at the site of a tissue injury and its action there creates a matrix which is ultimately broken down and replaced by healing tissue as part of the body's natural healing process. Thus it initially controls bleeding but remains firmly fixed in place until it is naturally biodegraded. Therefore it is capable of delivery chemotactic, growth promoting, and differentiation factors to induce both soft and hard tissue production or the innovation of undesirable proliferation. It may also used to deliver conventional pharmaceuticals in the form of antibiotics and chemotherapy drugs for prolonged periods.

A wide range of drugs can be incorporated into the composition for ultimate inclusion in the matrix which is formed at the site of administration for local action and/or systemic release. In particular, antibiotics, chemotherapeutics, peptide hormones, cytokines, antibodies, cell cycle regulators, chemokines, growth factors and secreted proteins may be incorporated in the matrix. The antibiotics may be from the fluoroquinolone class aminoglycocides such as hygromycin B, kanamycin and streptomycin, antifungal antibiotics such as amphotericin B, cyclohexamide, and nystatin, antineoplastic antibiotics, including mitomycin C, puromycin, and streptozocin, antitubercular antibiotics, including rifampicin and capreomycin, lactam antibiotics such as amoxicillin and penicillin, macrolide antibiotics, including nystatin and brefelden A, peptide antibiotics, including echinomycin and gramicicdin, tetracyclines, chloramphenicol and tunicamycin. Exemplary cytokines include, but are not limited to, the interleukins, beta-interferon, alpha-interferon, gamma-interferon, angiostatin, thrombospondin, endostatin, METH-1, METH-2, GM-CSF, G-CSF, M-CSF, tumor necrosis factor (TNF), and bone morphogenetic proteins (BMPs). Chemokines generally act as chemoattractants to recruit effector cells to the site of chemokine expression. Therefore the chemokines can recruit immune system components to the site of treatment. Suitable chemokines include, but are not limited to, RANTES, MCAF, MIP1-alpha, MIP1-Beta, and IP-10. Suitable growth factors include, but are not limited to, TGF-α, TGF-β, EGF, PDGF, FGFs, NGF, VEGF and KGF. Suitable secreted proteins include, but are not limited to, blood factors such as Factor VIII, Factor IX, von Willebrand Factor, and the like. Anti-cancer drugs have been demonstrated to show sustained release from a fibrin glue (Yoshida et al., 2000). Fibrin glues may also provide a slow release formulation for antibiotics when used in ocular surgery (Maronea et al., 1999). Furthermore fibrin glues have included antibiotics such as amikacin to prevent local graft infection (Nishimotol et al., 2004).

For the purposes of this specification it will be clearly understood that the word "comprising" means "including but not limited to", and that the word "comprises" has a corresponding meaning.

EXAMPLE 1

Photochemical Cross-Linking of Bovine Fibrinogen

A photochemical method was used to cross-link the soluble fibrinogen into a solid biomaterial and to effect the covalent cross-linking of the fibrinogen matrix to the proteins contained in the extracellular matrix surrounding the muscle tissue. Two small strips of bovine longissimus dorsi (LD) were dissected and the opposing surfaces coated in the sealant solution (200 mg/ml bovine fibrinogen was dissolved in PBS, with 2 mM [Ru(bpy)$_3$]Cl$_2$, 10 mM ammonium persulfate). Following 10 sec of irradiation, the two pieces of muscle were firmly attached. The light source chosen for the present study was a 600-W tungsten-halide source (2×300-W lamps; GE #38476). The spectral output showed a broad peak from 300 nm-1200 nm. Bovine fibrinogen (Fraction I, Sigma) (200 mg/ml) was dissolved in PBS, with 2 mM [Ru(bpy)$_3$]Cl$_2$, 10 mM ammonium persulfate) and photochemically cross-linked (600 W at 10 cm for 10 s).

EXAMPLE 2

Time of Light Exposure

Reactions contained 25 µg of bovine fibrinogen (Sigma); 2 mM [Ru(bpy)$_3$]Cl$_2$; 20 mM persulfate (Sodium salt) all in 25 µl PBS.

Figure 1:
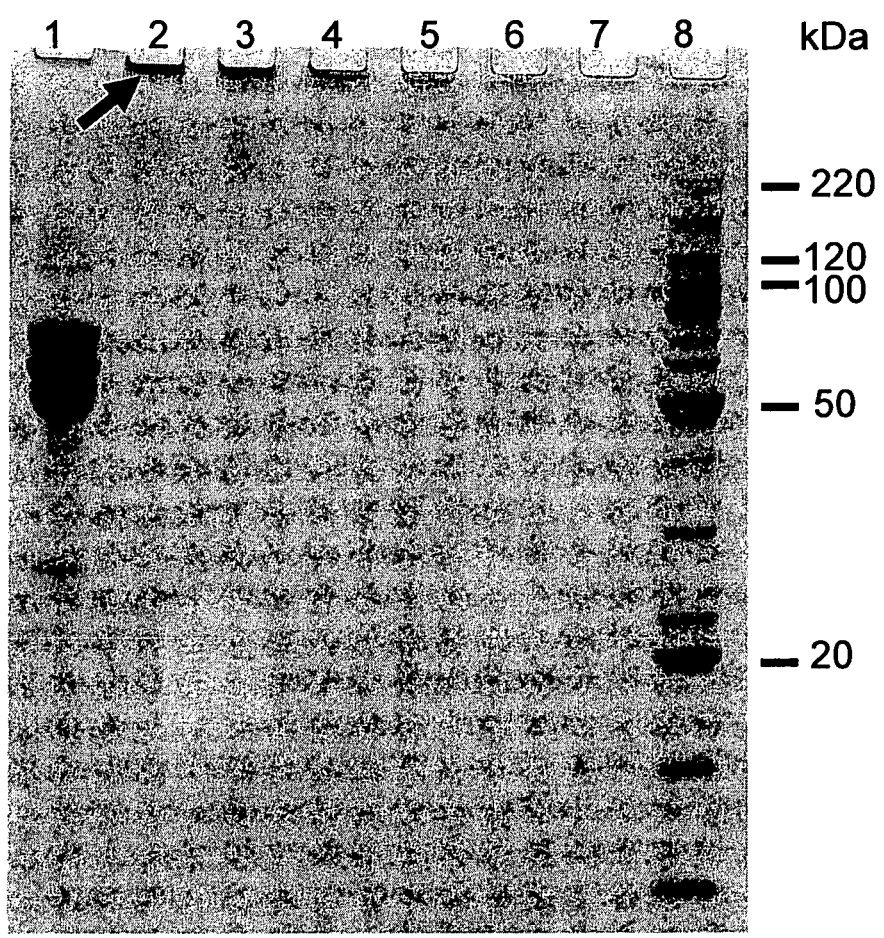
FIG. 1 shows a photograph of electrophoresis gel in which reaction mixtures containing 25 µg of bovine fibrinogen (Sigma); 2 mM [Ru(bpy)$_3$]Cl$_2$; 20 mM persulfate (Sodium salt) all in 25 µl PBS were exposed to 300 W incoherent light from Quartz Halogen dichroic source for various times.

Reactions were exposed to 300 W incoherent light from Quartz Halogen dichroic source for 1, 2, 5, 10, 30 and 60 seconds all resulted in the formation of high molecular weight, cross-linked fibrinogen polymers (FIG. 1).

EXAMPLE 3

Effect of Concentration of [Ru(bpy)$_3$]Cl$_2$

Reactions contained 25 µg of bovine fibrinogen (Sigma); 20 mM persulfate (Sodium salt) all in 25 µl PBS. Reactions were exposed to 300 W incoherent light from Quartz Halogen dichroic source for 1 min (FIG. 2) showing that the cross-linking reaction occurs across a range of [Ru (bpy)$_3$]Cl$_2$ concentrations.

EXAMPLE 4

Effect of Concentration of Persulfate

Reactions contained 25 µg of bovine fibrinogen (Sigma); 2 mM [Ru(bpy)$_3$]Cl$_2$ (Aldrich) all in 25 µl PBS. (SPS: sodium persulfate; APS: ammonium persulfate).

Reactions were exposed to 300 W incoherent light from Quartz Halogen dichroic source for 1 min (FIG. 3) demonstrating efficacy across a range of concentrations.

EXAMPLE 5

Demonstration of Alternative Electron Acceptors (Oxidants) Cross-Linking Protein Alternative oxidants for formation of protein hydrogels were investigated in the following tests. Fibrinogen derived from bovine plasma (Sigma cat# F8630) at a concentration of 5 mg/ml was used as the protein substrate for this investigation and was combined with the following different oxidants individually at a final reaction concentration of 10 mM.
1. Sodium Persulphate ($Na_2S_2O_8$)
2. Sodium Periodate ($NaIO_4$),
3. Vitamin B12 ($C_{62}H_{90}ClCoN_{13}O_{15}P$),
4. Ammonium cerium(IV) sulphate dehydrate ($Ce(NH_4)_4(SO_4)_4 \cdot 2H_2O$),
5. Ammonium cerium(IV) nitrate ($Ce(NH_4)_2(NO3)_6$
6. Oxalic acid ($HOOCCOOH \cdot 2H_2O$),
7. EDTA ($C_{30}H_{33}N_2O_8Na_3$).

Protein and oxidant were combined with 2 mM of the catalyst, Tris(2,2"-bipyridyl)dichlororuthenium(II) hexahydrate ($C_{30}H_{24}Cl2N_6Ru \cdot 6H_2O$) and immediately photoactivated for 60 seconds using a xenon 300 watt light source. Following this reaction, 0.5 µg of reacted protein was run under denaturing conditions on 10% BisTris SDS-PAGE. The gel was then stained using colloidal coomassie and effects of the cross-linking reaction determined. The results demonstrate that the oxidants; Sodium Persulphate and Sodium Periodate work strongly in cross-linking protein in the reaction. The other oxidants investigated also demonstrated efficacy in protein cross-linking but to a much lesser degree.

FIG. 4 illustrates the effects of the different oxidants on cross-linking of Fibrinogen at 5 mg/ml in PBS. In summary, the degree of cross-linking was determined by an increase in size of the protein relative to the protein standards (lanes S). Lane 1 shows no protein cross-linking of the Fibrinogen only reaction. Lanes 2, 4, 7 and 9; Ruthenium only, Ruthenium plus Vitamin B12, Ruthenium plus Oxalic acid and Ruthenium plus EDTA show slight cross-linking of the Fibrinogen. Lanes 5 and 6; Ruthenium plus Cerium Sulphate and Ruthenium plus Cerium Nitrate, show partial cross-linking of the Fibrinogen. Lanes 3 and 8; Sodium Persulphate and Sodium Periodate showed complete cross-linking of the Fibrinogen as demonstrated by the high molecular weight protein polymer remaining at the top of the gel.

EXAMPLE 6

Demonstration of Alternative Metal Ligand Complexes (Catalysts) for Cross-Linking Protein
Two Different Catalysts;
1) Tris(2,2"-bipyridyl)dichlororuthenium(II) hexahydrate ($C_{30}H_{24}Cl_2N_6Ru \cdot 6H_2O$) and
2) Hemin ($C_{34}H_{32}ClFeN_4O_4$)
were analysed in conjunction with the oxidants; Sodium Persulphate ($Na_2S_2O_8$) and Hydrogen Peroxide ($H_2O_2$) for their ability to cross-link Fibrinogen. The protein at 5 mg/ml was combined with the catalyst at a concentration of 1 mM and oxidant at 10 mM and immediately photoactivated using a xenon cool light source for 60 seconds. Following this reaction, 0.5 ug of reacted protein was run under denaturing conditions on a 10% BisTris SDS-PAGE. The gel was then stained using colloidal coomassie and effects of the cross-linking reaction determined. These results demonstrate that either Ruthenium or Hemin can be used as catalysts in cross-linking of proteins.

FIG. 5 illustrates the effects of the catalysts and oxidants on cross-linking of the Fibrinogen. Lane S is the protein standard. Lane 1; Fibrinogen only, shows no cross-linking. Lanes 3,4 and 7; Fibrinogen with Sodium Persulphate, Hydrogen Peroxide and Hemin only respectively showed no cross-linking. Lanes 2 and 6; Fibrinogen plus Ruthenium and Fibrinogen plus Ruthenium and Hydrogen Peroxide show slight cross-linking. Lane 5; Fibrinogen plus Ruthenium and Sodium Persulphate shows complete cross-linking of the protein as seen by the protein remaining at the top of the gel. Lanes 8 and 9; Fibrinogen plus Hemin and Sodium Persulphate and Fibrinogen plus Hemin and Hydrogen Peroxide demonstrate partial cross-linking of the protein as demonstrated by the smear of cross-linked protein polymer located at higher molecular weight locations and remaining at the top of the gel.

EXAMPLE 7

Photochemical Cross-Linking of Protein Solutions

A photochemical method was used to cross-link the protein solution into a solid article and to effect the covalent cross-linking of the proteins. An appropriate concentration of protein solution (typically 0.5-2% or more for collagen; typically 5% or more for other proteins, e.g. fibrinogen) in buffer solution is mixed with 2 mM $Ru(Bpy)_3$ and 20 mM persulphate salt (sodium, ammonium, potassium etc) and irradiated with white light (450 nm nominal wavelength) for at least 10 secs. to form the hydrogel. The light source chosen for the present study was a 600-W tungsten-halide source (2×300-W lamps; GE #38476). The spectral output showed a broad peak from 300 nm-1200 nm. This process is cell compatible. To form 3-dimensional structures the article can be cast or contained within transparent moulds.

EXAMPLE 8

Casting Various Shapes Using the PICUP Cross-Linking Method

A protein solution was mixed with $Ru(Bpy)_3$ to 2 mM final concentration and APS was added to 20 mM final concentration. The solution was mixed and placed into an appropriate transparent mould. The sample was irradiated using a 600 W tungsten-halogen lamp for 10 seconds at a distance of 15 cm. The solidified protein was then removed from the mould (FIGS. 9 and 10).

EXAMPLE 9

Degradation of and Tissue Response to Polymerised Fibrinogen Biopolymers In Vivo The solid fibrinogen biomaterial to be evaluated in a rat subcutaneous implant study was derived from a purified soluble fibrinogen protein which was cross-linked using a photochemical method involving Tris(bipyridyl) Ruthenium (II) chloride (2 mM final concentration) and ammonium persulphate (20 mM final concentration). The light source chosen for these studies was a 600-W tungsten-halide source (2×300-W lamps; GE #38476). The spectral output showed a broad peak from 300 nm-1200 nm.
Method
Animals 40, female, 8 week old, Wistar rats were purchased from the Animal Resource Centre, Canning Vale Wash. The rats were allowed to acclimatise to their new surroundings for 2 weeks prior to implantation of fibrinogen samples.
Anaesthesia Isoflurane, gaseous anaesthetic was used as the anaesthetic of choice because it has rapid induction and fast recovery. Each rat was induced with isoflurane (5%) in a mixture of oxygen (2 litres/minute). Induction of anaesthesia took approximately 30-60 seconds. Once the concentration of Isoflurane was reduced to 2% in a mixture of oxygen (2 litres/minute).
Subcutaneous Implantation The dorsum of the rat was shaved with clippers and the skin was disinfected with Iodine surgical scrub. A small incision was then made (approx 7 mm) through the dermis to the muscle layer. A pocket then created by parting the connective tissue between the dermis and muscle layer using blunt/blunt scissors. The sample plug was then gently placed in the pocket and positioned away from the initial incision point. The wound was closed using 29 mm wound clips. Groups 2, 4 & 5 had 2 subcutaneous biopolymers implanted per rat, each in a separate pocket. Group 3 only one biopolymer was implanted.

The samples implanted are as follows (suspended in PBS+ protease inhibitor cocktail):
1) Fibrinogen (Sigma fraction I) (cross-linked using photochemical method—the product is applied as a composition comprising fibrinogen, the Ru(II) catalyst and ammonium or sodium persulfate referred to hereinafter as "Fibrinogen-based Tissue Sealant" or "FBTS" and then irradiated)

Each plug (100 μl of 200 mg/ml) of cross-linked fibrinogen was conical in shape: 4 mm on base, 1 mm at top and 5-6 mm high. All plugs were beige/brown in colour.

The height (width) and length of each polymer was measured using digital callipers weekly for the first 4 weeks and then every 2 weeks for the remainder of the experiment.

One week after implantation of the fibrinogen samples no swelling was observed (except one rat where the wound is most likely infected). All animals seem normal in behaviour and appearance.

Two weeks after implantation all plugs that had increased in size were similar in size to that implanted or had slightly reduced. No inflammation was observed.

Three weeks after implantation 2 rats from each group were killed. No gross pathology was noted in any organ and all organs (heart, liver, spleen, lung and kidney) were all histologically normal. Most plugs appeared to have started to degrade/be reabsorbed. Most had a thin capsule covering the plug. The fibrinogen plugs were flattened. No macroscopic/gross inflammation was noted at any of the implantation sites or around any of the plugs.

Eight weeks: 2 rats were killed from each group. The fibrinogen plugs had reduced in size and were spherical in shape. One animal from the fibrinogen group had hardened kidneys with an enlarged spleen—possible carcinoma of the kidneys, however this was unrelated to the implant.

Eighteen weeks: 2 rats from each group were killed. No plugs were seen in animals implanted Fibrinogen. The plugs had fully degraded/been reabsorbed. There was no gross pathology seen in any of the major organs from all animals.

Thirty six weeks—Study Terminated. The study was terminated. The implanted plugs from all groups had fully degraded or been reabsorbed. No gross pathology was noted in any of the major organs from any animal.

EXAMPLE 10

Photochemical Cross-Linking of Gelatin and Acid-Denatured BSA

Gelatin (Sigma) was dissolved at 65° C. in PBS at the concentrations shown in Table 1.

BSA was dissolved in 60 mM sodium acetate pH 4.0 at room temperature at either 20% or 10% final concentration for adhesive testing.

Ruthenium tris-bipyridyl chloride (RuBpy$_3$Cl) and sodium persulphate (NaS$_2$O$_8$) were prepared in sterile water at 50 mM and 500 mM, respectively. These reagents were added to final concentrations shown in Table 1.

By way of comparison, Tisseel (Duo 500 1 ml) was obtained from Baxter (NSW Australia). 100 μl of Tisseel tissue adhesive solution was added to one surface of bovine amnion and the two opposing amnion surfaces brought together and held under light pressure for 15 min at room temperature prior to tensile testing.

EXAMPLE 11

Tensile Testing

A perspex uniaxial tensile testing μg was constructed to measure the adhesive strength of adherent tissue surfaces. Bovine amnion was prepared following separation of the chorion from fresh amniotic sac abattoir specimens. The pieces of amnion were cut into 5 cm×5 cm samples and fixed over the top surface via rubber o-rings to the test jig. 100 μl of tissue adhesive solution was added to one surface and the two opposing surfaces brought together and immediately illuminated using a 600 W tungsten halide light source. The light source was a 600-W tungsten-halide lamp (2×300-W lamps; GE #38476). The spectral output showed a broad peak from 300 nm-1200 nm. Lead weight was added progressively until failure. The breaking stress was measured in kPa, and calculated using a cross-sectional area of 1.76 cm$^2$.

TABLE 1

| Tissue adhesive strength | |
|---|---|
| Type of denatured protein (crosslinking conditions) | Maximum Adhesive strength breaking stress (kPa) |
| Gelatin - Bovine Type B - 15% high bloom (Sigma G9391) 2 mM Ru(Bpy)$_3$, 20 mM SPS | 92.8 |
| Gelatin - Bovine Type B - 15% low bloom (Sigma G6650) 2 mM Ru(Bpy)$_3$, 20 mM SPS | 87.1 |
| Gelatin - Porcine Type A - 15% high bloom (Sigma G2500) 2 mM Ru(Bpy)$_3$, 20 mM SPS | 75.2 |
| Gelatin - Porcine Type A - 15% low bloom (Sigma G 6144) 2 mM Ru(Bpy)$_3$, 20 mM SPS | 81.8 |
| Gelatin - Porcine Type A - 25% low bloom (Sigma G 6144) 2 mM Ru(Bpy)$_3$, 20 mM SPS | 81.5 |
| Gelatin - Cold water fish skin - 40% (Sigma G7041) 2 mM Ru(Bpy)$_3$, 40 mM SPS | 81.1 |
| Gelatin - Cold water fish skin - 30% (Sigma G7041) 2 mM Ru(Bpy)$_3$, 40 mM SPS | 73.3 |
| Gelatin - Cold water fish skin - 30% (Sigma G7041) 2 mM Ru(Bpy)$_3$, 20 mM SPS | 67.5 |
| BSA 20% - acid denatured (60 mM sodium acetate pH 4.0); 2 mM Ru(Bpy)$_3$, 20 mM SPS | ~52 |
| BSA 10% - acid denatured (60 mM sodium acetate pH 4.0); 2 mM Ru(Bpy)$_3$, 20 mM SPS | 52.7 |
| Tisseel ™ (Baxter) control | 18.8 |

Table 1 shows the adhesive bond strengths of various denatured proteins used as tissue adhesives in the current application. Data are presented alongside adhesive strength obtained using a commercial fibrin glue (Tisseel). All of the denatured protein samples tested showed higher maximum breaking stress than Tisseel.

EXAMPLE 12

Hydrolysis of Gelatin 1 mg of gelatin was dissolved in 1 ml of 6N Hydrochloric acid containing 0.02% Phenol. Sample is then heated at 110° C. for 24 hours. At the end of the incubation period samples are dried and ready for the derivatisation process.

Derivatisation of Amino Acids

Reconstitute hydrolysed sample in 25 μl of Ethanol: Water: Triethylamine (2:2:1) and mix. Dry samples under vacuum at 60° C. After samples are dry add 25 μl of Ethanol: Water: Triethylamine:Phenylisocyanate (7:1:1:1) and mix. Incubate the samples at room temperature for 30 minutes and then dry under vacuum at 60° C. The samples are then reconstituted in 500 μl Mobile phase A ready for HPLC analysis.

High Performance Liquid Chromatography of Amino Acids Conditions

Column: Phenomenex BF 4252-EO, Luna 5 μm C18 (2), 150×6.0 mm.
Wavelength: 254 nm
Oven Temperature: 40° C.
Mobile Phase A: 0.14M Sodium Acetate, 0.05% Triethylamine, pH 6.5
Mobile Phase B: 60% Acetonitrile
Injection Volume: 25 μl

TABLE 2

Amino acid composition (in mol % or Area %) of gelatin (bovine skin, type B) not crosslinked or crosslinked using photochemical crosslinking described above.

| Amino Acid | Mol %* | Area % Gelatin | Area % Gelatin, Ru, Ru not leached | Area % Gelatin, Ru, Ru leached† |
|---|---|---|---|---|
| Asp | 2.8 | 3.3 | 2.3 | 2.8 |
| Thr | 1.9 | 1.4 | 1.4 | 1.4 |
| Ser | 2.8 | 3 | 3.1 | 2.9 |
| Glu | 7.6 | 6.1 | 5.7 | 5.4 |
| Pro | 12.3 | 15.2 | 15.1 | 14.9 |
| Gly | 32.3 | 31.1 | 34.2 | 32.7 |
| Ala | 14.2 | 11.1 | 11.3 | 10.9 |
| Val | 2.2 | 2 | 2.1 | 2.0 |
| Cys | — | — | — | — |
| Met | 0.9 | 0 | 0.2 | 0 |
| Ile | 1.9 | 1.2 | 1.1 | 2.2 |
| Leu | 2.8 | 2.3 | 2.1 | 2.1 |
| Tyr | 0.9 | 0.3 | 0 | 0 |
| Phe | 1.9 | 1.4 | 1.4 | 1.4 |
| Lys | 2.8 | 5.2 | 5.7 | 8.7 |
| His | 0.9 | 0.4 | 0.4 | 0.4 |
| Arg | 3.8 | 4.7 | 4.2 | 2.4 |
| OH-Pro | 6.6 | 11 | 9.9 | 10.8 |
| OH-Lys | 0.9 | — | — | — |

Table 2 shows the amino acid composition of bovine gelatin measured before and after photochemical crosslinking. The loss of a measurable tyrosine peak in the crosslinked sample supports the role of tyrosine in the crosslinking mechanism.

EXAMPLE 13

Stabilisation of gelatin beads

Beads were made from 25% w/v A-type gelatin (175 g Bloom) heated to 50 C to dissolve. After cooling to 37° C., sodium persulfate (10 mM final concentration) and tris bipyridyl ruthenium (2 mM final concentration) were added in the dark and the mixture dispersed by addition with an 18G needle at 10% v/v in olive oil at 50° C. by rapid stirring, while maintained in the dark. After 30 min, the emulsion was transferred to 20° C. and illuminated while stirred twice for 2 min. at 15 min intervals and then every 30 min for a further 5 hours using a 500 W quartz-halogen lamp. Beads were separated by sedimentation followed by extraction with ethanol and/or acetone. The effective stabilisation of the beads was shown after rehydration and addition to water at 56° C. After 16 hr, no dissolution nor shape changes of the beads was observed.

EXAMPLE 14

Delivery of cross linked protein using a sponge support. Fibracol collagen sponge impregnated with 15% bovine gelatin (with Ru(Bpy)$_3$ and SPS)

Method

The adhesive strength of photochemically cured gelatin, delivered in a sponge was assessed by impregnating a 176 mm$^2$ disc of Fibracol Plus collagen sponge (Ethicon) with 500 μl of 15% Bovine gelatin (Sigma G9391) dissolved in PBS. The adhesive bond strength of this formulation was measured using a tensile testing jig to assess the adhesive strength to bovine amnion membrane.

The gelatin solution was maintained at 45° C. in a water bath, the [Ru(Bpy)$_3$]$^{2+}$ was added to 2 mM and sodium persulphate added to 20 mM final concentration. The solution was mixed thoroughly and the Fibracol Plus sponge membrane then thoroughly impregnated with the protein mixture. The soaked membrane was then placed between the amnion membranes and the upper half of the jig was lowered to meet the lower half with a small force (~250 gf) applied. The assembled test jig was illuminated for 60 seconds using a 300 W xenon lamp. Samples were tested for tensile stress at break in triplicate.

Results
1. 15.4N
2. 12.95N
3. 10.72N

Mean=13.02N/176 mm$^2$
Maximum tensile stress at break=73.7 kPa

These data demonstrate that photochemically cross-linked gelatin can be delivered using an inert carrier such as a collagen sponge.

EXAMPLE 15

Tensile Testing of Photochemically-Cross-Linked Fibrinogen

Tensile tests were carried out on cross-linked fibrinogen in phosphate-buffered saline (PBS) buffer on an Instron Tensile Tester (model 4500) at a rate of 5 mm/min and a temperature of 21° C. The swollen dumbbell-shaped strip samples (30 mm×4 mm×1 mm) had a gauge length of 8 mm and strain was increased until failure occurred (FIG. 19). The elastic modulus (E) was measured at 20%, 40% and 50% strain, yielding figures of 77 kPa, 85 kPa and 87 kPa respectively (FIG. 20). These measurements of Young's Modulus are similar to data obtained from studies using two commercial fibrin-based tissue sealants. The extension to break (Eb) was 135% and the ultimate tensile strength UTS was 141 kPa. Velada et al (2002) compared the mean tensile strength of several commercial fibrin sealants (Vivostat, Tussucol and Beriplast) and these were found to be in the range 38 kPa to 55 kPa.

The resilience of the cross-linked fibrinogen hydrogel was determined at 10% and 20% strain and yielded a figure of 70.7%, considerably less than resilin (97%), but illustrating that cross-linked fibrinogen hydrogels consist of elastic domains. Importantly, the extension to break was 135%, illustrating the extensibility of the photochemically cross-linked fibrinogen biomaterial. Velada et al reported the mean extension to break of commercial fibrin sealants to be 103%±13% but tensile strength varied by 2-5-fold with fibrinogen concentrations in the range 25-100 mg/ml.

EXAMPLE 16

In Vivo Study of Fibrinogen Scaffold

Porous hydrogel scaffolds of photo-crosslinked fibrinogen, seeded with cells, were implanted subcutaneously into nude mice. The viability of the implanted cells and integration of the scaffolds with surrounding tissue were assessed at 2 and 4 weeks after implantation of the scaffolds.

Materials and Methods

The scaffolds contained 60 mg/ml bovine fibrinogen in Dulbecco's Modified Eagle's Medium. The scaffolds also contained 50 µg/ml bovine catalase and 1% hydrogen peroxide to induce foaming and hence produce a porous matrix, and 2 mM ruthenium and 20 mM sodium persulfate to achieve photo-crosslinking during exposure to blue light for 30 s. The scaffolds were seeded with $2\times10^6$ cells/ml of C2 C12 mouse myoblasts. The cell-containing scaffolds were cultivated for three days in vitro, then surgically implanted into 8 week old nude mice. Two implants were placed subcutaneously in each animal, one on either side of the mid-dorsal line. Animals were sacrificed at 2 weeks (three animals) and 4 weeks (two animals) post-surgery and the scaffolds and surrounding tissue were removed. Samples were examined macroscopically and histologically.

Results

At 2 and 4 weeks post-surgery, the implanted scaffolds were well integrated into surrounding tissue and all organs were normal. Histological examination showed that the implanted C2 C12 myoblasts had survived and proliferated, as clearly evidenced by the differentiation of several myoblasts into multinucleated, thickened and elongated myotubes. There was also microscopic evidence of the integration of multiple new blood vessels into the scaffold (FIG. 22).

This example demonstrates that scaffolds containing cells have been successfully implanted into nude mice, with evidence of survival, proliferation and differentiation of the originally implanted cells. There is also clear evidence of integration of the scaffolds with surrounding tissue as well as vascularisation of the implanted scaffolds.

EXAMPLE 17

Stabilization of a Thrombin Induced Clot by Crosslinking Using a Photochemical Method Fibrinogen (Sigma Fraction1) was dissolved at either 5 mg/ml or 50 mg/ml in phosphate-buffered saline (Dulbecco's PBS without Ca & Mg). Thrombin (Sigma—from bovine plasma, 34.8 U/mg solid) was prepared as a 20 mg/ml solution in PBS. Ruthenium tris-bipyridyl chloride ($RuBpy_3Cl$) and sodium persulphate ($NaS_2O_8$) were prepared in sterile water at 50 mM and 500 mM, respectively.

FIG. 21 shows the result of treating two concentrations of fibrinogen for 2 minutes at room temperature with thrombin. Panel A shows a clot formed from a 5 mg/ml solution of fibrinogen (similar to the concentration of fibrinogen in blood—ref: Weisel J W. Fibrinogen and fibrin. Adv Protein Chem. 2005; 70:247-99.). Panel B shows a stiffer clot formed from a 50 mg/ml solution of fibrinogen. Both fibrinogen solutions were treated with 10.5 U of thrombin at room temperature. Both clots were completely soluble in 2.5% acetic acid within 2 minutes at room temperature. Panel C shows photochemically crosslinked fibrin (samples treated as in A, but 2 mM ruthenium tris-bipyridyl and 20 mM sodium persulphate added simultaneously with thrombin in the dark). The samples were then illuminated with white light (600 W tungsten halide lamp) for 10 seconds. Samples were subsequently soaked in 2.5% acetic acid ("5" is fibrinogen at 5 mg/ml; "50" is fibrinogen at 50 mg/ml) and were insoluble as shown. Panel D shows a fibrinogen sample (5 mg/ml) treated with 2 mM ruthenium tris-bipyridyl and 20 mM sodium persulphate, added simultaneously with thrombin in the dark. The fibrin clot was subsequently transferred in the dark to a solution of 2.5% acetic acid. After 2 minutes at room temperature, the clot dissolved completely, demonstrating that, without illumination, no covalent crosslinking occurred in the fibrin clot.

The data (FIG. 21) demonstrates that following visible light illumination via a photochemical reaction, addition of ruthenium tris-bipyridyl and sodium persulphate to thrombin stabilizes the clot formed from fibrinogen. This reaction is independent of any action of Factor XIII. A clot formed via the action of thrombin, in vivo, would similarly be covalently crosslinked via this photochemical process and that this clot will be covalently bonded to the protein components in the ECM, thus forming a more robust clot at the wound site.

REFERENCES

The disclosure of the following documents is incorporated herein by reference:

Barnes C P, Smith M J, Bowlin G L, Sell S A, Tang T, Matthews J A, Simpson D G, Nimtz J C "Feasibility of Electrospinning the Globular Proteins Hemoglobin and Myoglobin" Journal of Engineered Fibers and Fabrics Vol 1 No. 2, 16-29 (2006)

Brown, K C and Kodadek, T Met Ions Biol Syst. 2001; 38:351-84. "Protein cross-linking mediated by metal ion complexes"

Dickneite, G., H. J. Metzner, M. Kroez, et al. "The Importance of Factor XIII as a Component of Fibrin Sealants." Journal of Surgical Research 107 (October 2002): 186-195.

Dodd, R. A., R. Cornwell, N. E. Holm, et al. "The Vivostat Application System: A Comparison with Conventional Fibrin Sealant Application Systems." Technology and Health Care 10 (2002): 401-411.

D A. Fancy and T. Kodadek "Chemistry for the analysis of protein-protein interactions: Rapid and efficient cross-linking triggered by long wavelength light." Proc. Natl. Acad. Sci. Vol. 96, pp. 6020-6024, May 1999

David A Fancy, Carilee Denison, Kyonghee Kim, Yueqing Xie, Terra Holdeman, Frank Amini and Thomas Kodadek "Scope, limitations and mechanistic aspects of the photo-induced cross-linking of proteins by water-soluble metal complexes" Chemistry & Biology (2000) 7:697-708

Furst W, Banerjee A, Redl H. Comparison of structure, strength and cytocompatibility of a fibrin matrix supplemented either with tranexamic acid or aprotinin. J Biomed Mater Res B Appl Biomater. (2007) 82:109-14

Jackson, M. R. "Fibrin Sealants in Surgical Practice: An Overview." American Journal of Surgery 182 (August 2001) (2 Suppl): 1S-7S.

Kodadek T, Isabelle Duroux-Richard and Jean-Claude Bonnafous, "Techniques: Oxidative cross-linking as an emergent tool for the analysis of receptor-mediated signalling events" TRENDS in Pharmacological Sciences Vol. 26 No. 4 Apr. 2005

Khadem, J., Veloso, A. A., Tolentino, F. T., Hasan, T. and Hamblin, M. R., "Photodynamic Tissue Adhesion with Chlorin$_{e6}$, Protein Conjugates". IOVS, December 1999, Vol. 40, No. 13.

Lee, K-C, Park, S-K and Lee, K-S (1991) neurosurgical applications of fibrin sealants. 9$^{th}$ Annual congress of the world society of cardio-thoracic surgeons; November 1999, Lisbon, Spain.

Makogonenko E, Ingham K C, Medved L. Interaction of the fibronectin COOH-terminal Fib-2 regions with fibrin: further characterization and localization of the Fib-2-binding sites. Biochemistry. (2007) May 8; 46(18):5418-26. Epub 2007 Apr. 11

Mankad, P. S., and M. Codispoti. "The Role of Fibrin Sealants in Hemostasis." American Journal of Surgery 182 (August 2001) (2 Suppl): 21S-28S.

Maronea Piero, Monzillob Vincenza, Segua Catia, Antoniazzic Elena, "Antibiotic-Impregnated Fibrin Glue in Ocular Surgery: In vitro Antibacterial Activity", Ophthalmologica 1999; 213:12-15.

Matras, H (1985) Fibrin seal: the state of the art. J Oral Maxillofac Surg 43: 605-611.

McManus, M, Sell S A, Espy P G, Koo, H P and Bowlin G L (2006) "On the Road to in situ Tissue Regeneration: A Tissue Engineered Nanofiber Fibrinogen- Polydioxanone Composite Matrix" Proceedings of Mid-Atlantic section of the American Urological Association Annual Meeting, 2006

Milne, A A, Murphy, W G, Reading, S J and Ruckley, C V (1995) Fibrin sealant reduces suture line bleeding during carotid endarterectomy: a randomised trial. Eur J Endovasc Surg 10: 91-94

Morikawa, T. "Tissue Sealing." American Journal of Surgery 182 (August 2001) (2 Suppl): 29S-35S.

Mosesson M W, Fibrinogen and fibrin structure and functions. J Thromb Haemost. (2005) 3:1894-904;

Mosesson M W, Siebenlist K R, Meh D A. The structure and biological features of fibrinogen and fibrin. Ann N Y Acad. Sci. 2001; 936:11-30).

Nishimotol Kazuo, Yamamura Keiko, Fukase Fumiaki, Kobayashil Masayoshi, Nishikimil Naomichi and Komoril Kimihiro, "Subcutaneous tissue release of amikacin from a fibrin glue/polyurethane graft", Journal of Infection and Chemotherapy; Vol. 10, No. 2 (2004) pages 101-104.

Velada J L, Hollingsbee D A, Menzies A R, Cornwell R, Dodd R A. Reproducibility of the mechanical properties of Vivostat system patient-derived fibrin sealant. Biomaterials. 2002 May; 23(10):2249-54.

Yoshida H, Yamaoka, Y., Shinoyama M., Biol Pharm Bull. 2000; pages 371-374 "Novel drug delivery system using autologous fibrin glue-release properties of anti cancer drugs", Department of Pharmacy, Yamaguchi University Hospital, Ube, Japan.

The invention claimed is:

1. A method of crosslinking an at least partially denatured protein for use as a tissue sealant, the method comprising:
   the step of irradiating a photoactivatable metal-ligand complex and an electron acceptor in the presence of the at least partially denatured protein,
   thereby initiating a cross-linking reaction to form a 3-diminensional matrix of the tissue sealant.

2. The method as claimed in claim 1 wherein denaturation of the protein occurs as the result of application of heat, physical or mechanical agitation or acid/alkali treatment or as a result of chemical modification.

3. The method as claimed in claim 1 wherein the denatured protein is gelatin.

4. The method as claimed in claim 1 wherein the electron acceptor is peracid or an organic acid.

5. The method as claimed in claim 4 wherein the electron acceptor is persulfate.

6. The method as claimed in claim 5 wherein the electron acceptor is ammonium persulfate or sodium persulfate.

7. The method as claimed in claim 1 wherein the photoactivatable metal-ligand is an Ru(II) complex.

8. The method as claimed in claim 7 wherein the complex is an Ru(II) bipyridyl complex.

9. The method as claimed in claim 8 wherein the complex is a tris(bipyridyl) Ru(II) complex.

10. A method of joining and/or sealing at least one substrate, comprising the steps of:
    (1) applying an at least partially denatured protein solution, a photoactivatable metal ligand complex and an electron acceptor to at least one substrate;
    (2) irradiating said material to photoactivate the photoactivatable metal-ligand complex;
    thereby initiating a cross-linking reaction to adhere or join said substrate to an adjacent substrate.

11. The method as claimed in claim 10 wherein the protein is gelatin.

12. A method of joining and/or sealing tissues in a surgical procedure or medical treatment, comprising the steps of:
    (1) applying to a tissue portion a photoactivatable metal-ligand complex and an electron acceptor and an at least partially denatured protein
    (2) irradiating said tissue portion to photoactivate the photoactivatable metal-ligand complex;
    thereby initiating a cross-linking reaction between (a) one or more endogenous proteins and (b) said at least partially denatured protein to seal said tissue portion or join said tissue portion to an adjacent tissue portion and
    wherein said at least partially denatured protein has been rendered more susceptible to photochemical cross-linking compared to its native state.

13. The method of claim 10, wherein the cross-linking reaction further comprises adhering or joining said substrate to an adjacent substrate as an implant, tissue sealant, or tissue scaffold.

14. The method of claim 12, wherein the cross-linking reaction further comprises sealing or joining said tissue portion to said adjacent tissue portion as an implant, tissue sealant, or tissue scaffold.

* * * * *